(12) United States Patent
Jianmin

(10) Patent No.: US 6,596,924 B1
(45) Date of Patent: Jul. 22, 2003

(54) GRAFT ANIMAL MODEL FOR HIGH INDUCTION OF PAPILLOMAS, THE PROPAGATION OF PAPILLOMAVIRUS AND EVALUATION OF CANDIDATE THERAPEUTIC AGENTS

(75) Inventor: Duan Jianmin, Chomedey (CA)

(73) Assignee: Boehringer Ingelheim (Canada) Ltd., Laval (CA)

( * ) Notice: Subject to any disclaimer, the term of this patent is extended or adjusted under 35 U.S.C. 154(b) by 0 days.

(21) Appl. No.: 09/465,666

(22) Filed: Dec. 17, 1999

Related U.S. Application Data
(60) Provisional application No. 60/114,642, filed on Jan. 4, 1999.

(51) Int. Cl.[7] ..................... A01K 67/033; A61K 39/12; A61K 31/00; C12N 15/63
(52) U.S. Cl. ............................. 800/9; 800/8; 800/435; 800/320.1; 800/424; 800/204.1; 800/514; 800/44
(58) Field of Search ........................... 800/8, 9; 514/44; 424/204.1; 435/320.1

(56) References Cited

U.S. PATENT DOCUMENTS

| | | |
|---|---|---|
| 4,814,268 A | 3/1989 | Kreider et al. |
| 5,811,632 A | 9/1998 | Brandsma |

OTHER PUBLICATIONS

Bonnez W Et Al: "Propagation of Human Papillomavirus Type 11 in Human Xenografts using the Severe Combined Immunodeficiency (SCID) Mouse and Comparison to the Nude Mouse Model" Virology, Jan 1, 1993 197:455–458.

Bonnez W Et Al: "Isolation and propagation of human papillomavirus type 16 in human xenografts implanted in the severe combined immunodeficiencymouse" Journal of Virology, Jun. 1998 72(6):5256–5261.

Howett M. Et Al: "Human xenografts: a model system for human papillomavirus infection" Intervirology, 1990, 31:109–115.

Kreider JW Et Al: "Primary neoplastic transformation in vivo of xenogeneic skin grafts on nude mice", Cancer Research, Jan. 1979, 39:273–276.

*Primary Examiner*—Anne M. Wehbe'
(74) *Attorney, Agent, or Firm*—Robert P. Raymond; Susan K. Pocchiari; Mary-Ellen M. Devlin

(57) ABSTRACT

The present invention relates to a graft animal model for propagating papilloma virus and for evaluating and testing candidate therapeutic agents against papilloma virus. The animal model comprises, a recipient animal engrafted with injured skin graft infected with a host-specific papilloma virus (PV). The grafted skin, having demonstrable papillomas supports the propagation of its host-specific PV. The invention particularly relates to a xenograft animal model for hosting and propagating human papillomavirus (HPV), thereby providing a means for generating infectious and passaging HPV suspensions, and for screening candidate therapeutic agents against HPV. The invention additionally relates to a novel method for generating the xenograft human animal model.

21 Claims, 14 Drawing Sheets

(4 of 14 Drawing Sheet(s) Filed in Color)

A.

B.

A. Typical histology   B. In situ hybridization   C. Immunohistochemistry

A.

B.

GRAFT ANIMAL MODEL FOR HIGH INDUCTION OF PAPILLOMAS, THE PROPAGATION OF PAPILLOMAVIRUS AND EVALUATION OF CANDIDATE THERAPEUTIC AGENTS

This application claims the benefit of Provisional Application Serial No. 60/114,642 filed Jan. 4, 1999.

FIELD OF THE INVENTION

The present invention relates to a graft animal model for propagating HPV and for evaluating and testing candidate therapeutic agents against HPV. The animal model comprises, a recipient animal engrafted with injured skin graft infected with a host-specific papilloma virus (PV). The grafted skin, having demonstrable papillomas supports the propagation of its host-specific PV. The invention particularly relates to a highly reproducible xenograft animal model for hosting and propagating human papillomavirus, thereby providing a means for generating infectious human PV suspensions and for passaging papillomavirus. The invention additionally relates to a novel method for generating the xenograft human animal model.

BACKGROUND OF THE INVENTION

Papillomaviruses (PV) are non-enveloped DNA viruses that induce hyperproliferative lesions of the epithelia. The papillomaviruses are widespread in nature and have been recognized in higher vertebrates. Viruses have been characterized, amongst others, from humans, cattle, rabbits, horses, and dogs. The first papillomavirus was described in 1933 as cottontail rabbit papillomavirus (CRPV). Since then, the cottontail rabbit as well as bovine papillomavirus type 1 (BPV-1) have served as experimental prototypes for studies on papillomaviruses. Most animal papillomaviruses are associated with purely epithelial proliferative lesions, and most lesions in animals are cutaneous. In the human there are more than 75 types papillomavirus (HPV) that have been identified and they have been catalogued by site of infection: cutaneous epithelium and mucosal epithelium (oral and genital mucosa). The cutaneous-related diseases include flat warts, plantar warts, etc. The mucosal-related diseases include laryngeal papillomas and anogenital diseases comprising cervical carcinomas (Fields, 1996, Virology, 3rd ed. Lippincott—Raven Pub., Philadelphia, N.Y.).

There are more than 25 HPV types that are implicated in anogenital diseases, these are grouped into "low risk" and "high risk" types. The low risk types include HPV type 6, type 11 and type 13 and induce mostly benign lesions such as condyloma acuminata (genital warts) and low grade squamous intraepithelial lesions (SIL). In the United States there are 5 million people with genital warts of which 90% is attributed to HPV-6 and HPV-11. About 90% of SIL are also caused by low risk types 6 and 11. The other 10% of SIL are caused by high risk HPVs.

The high risk types papillomaviruses are associated with high grade SIL and cervical cancer and include most frequently HPV types 16, 18, 31, 33, 35, 45, 52, and 58. The progression from low-grade SIL to high-grade SIL is much more frequent for lesions that contain high risk HPV-16 and -18 as compared to those that contain low risk HPV types. In addition, only four HPV types are detected frequently in cervical cancer (types 16, 18, 31 and 45). About 500,000 new cases of invasive cancer of the cervix are diagnosed annually worldwide (Fields, 1996, supra).

Treatments for genital warts include physical removal such as cryotherapy, $CO_2$ laser, electrosurgery, or surgical excision. Cytotoxic agents may also be used such as trichloroacetic acid (TCA), podophyllin or podofilox. Immunotherapy is also available such as Interferon or Imiquimod. These treatments are not completely effective in eliminating all viral particles and there is either a high cost incurred or uncomfortable side effects related thereto. In fact, there are currently no effective antiviral treatments for HPV infection, since with all current therapies recurrent warts are common (Beutner & Ferenczy, 1997, Amer. J. Med., 102(5A): 28–37).

The life cycle of HPV is closely coupled to keratinocyte differentiation. Infection is believed to occur at a site of tissue disruption in the basal epithelium. Unlike normal cells, cellular division continues as the cell undergoes vertical differentiation. As the infected cells undergo progressive differentiation the viral copy number and viral gene expression increase, with the eventual late gene expression and virion assembly in terminally differentiated keratinocytes and the release of viral particles (Fields, 1996, supra).

Papillomaviruses are fastidious viruses that cannot be propagated in vitro. As such, the virus requires a host-specific animal for growth. The ineffectiveness of the current methods to treat PV infections has demonstrated the need to identify new therapeutic agents as a means to prevent and treat HPV infections. The success of developing candidate therapeutic agents to combat papillomavirus has been limited in part due to difficulties including, propagating the virus, obtaining sufficient infectious viral particles and the lack of a good in-vivo model to evaluate the effectiveness of candidate therapeutic agents. Attempts to overcome these difficulties have been addressed by generating xenograft animal models for human papillomavirus. However, all the models known in the prior art have had limited success in overcoming these difficulties.

The ideal animal model is described as having the following attributes: being widely available, easy to handle and maintain in a laboratory, large enough to provide tissue samples, able to induce and form papilloma lesions that are comparable to those in humans, the papillomas should be readily accessible for treatment, and able to yield a large amount of infectious viral particles (Stanley, et al., 1997, Antiviral Chemistry & Chemotherapy, 8(5):381–400).

In U.S. Pat. Nos. 4,814,268 and 5,071,757 (Kreider et al.), human skin tissue subjected to human papillomavirus was grafted under the renal capsule of athymic mice. This is a complex procedure which requires surgical refinement. The graft is allowed to remain in the animal until recoverable quantities of the virus are produced. Examination of the graft site and recovery of viral particles requires the animals to be killed. The infectivity of the recovered viral particles from the graft site was reported to be only at a $10^{-2}$ dilution. More importantly, since the papillomas formed are not visible, evaluation of therapeutic agents necessitates sacrificing the animal. Subsequent attempts by this group (Kowett et al., 1990, Int. Virology, 31:109–115) to replicate these published results, harvesting infectious viral stock capable of infecting other animal models, have failed. The authors hypothesized that the first wart tissue collected from patients and used to infect an animal model probably contains more infectious virions and is thus successful in initiating papilloma infection in the xenograft animal.

Bonnez W. et al. (1993, Virology 197:455–458) described human foreskin infected in vitro with HPV type 11, implanted under the renal capsule, peritoneum and subcutaneous in SCID mice. Only 58% of the grafts showed signs of HPV infections. In the subcutaneous implanted grafts, only 25% were positive for HPV by immunocytochemistry and RT-PCR. The resultant subcutaneous papillomas were not serially passaged or harvested.

Brandsma J. L. et al. (1995, J. of Vir. 69:2716–2721) and U.S. Pat. No. 5,811,632, describe the delivery of HPV type 16 genomic DNA to human foreskin engrafted onto SCID mice. In total 16 grafts were inoculated with naked HPV DNA, eight inoculated pre-engrafting and eight post-engrafting. Only two grafts inoculated post-grafting appeared to develop signs of HPV infection. However these two prior art documents do not teach harvesting infectious viral particles or the passaging of papillomavirus.

Sexton C. J. et al. (1995, J. of Gen. Vir. 76:3107–3112) described a grafting method whereby a glass cover slip was first inserted into the graft site of a SCID mouse for one to two weeks. This is replaced with a silicone grafting chamber in which benign wart tissue was placed. After five weeks, macroscopic warts developed. Attempts to graft the wart tissue resulted in hyperproliferative human epithelium devoid of viral infection. Thus serial passaging of these warts and harvesting infectious particles are not taught.

Bonnez W. et al. (1998, J. Virol. 72:5256–5261) reported the isolation and propagation of HPV-16. The virus was isolated from clinical samples and used to infect human foreskin prior to subcutaneous implantation into SCID mice. The sites were prepared by inserting glass cover slips at the graft sites two weeks prior to engrafting the infected foreskin. The lesions at the graft sites were exposed four weeks after engrafting and the animals sacrificed 24 weeks after engrafting. Only three of the five grafts showed small papillomas. The virions from these papillomas were harvested and used to inoculate a second set of xenografted human tissue. In this second set of animals 60 grafts were attempted, the resultant lesions were not exposed and the animals were sacrificed 16 weeks after engrafting. Of the 60 grafts, 34 were positive for the presence of HPV DNA and only 1 was positive for HPV capsid by immunochemistry. This prior art does not teach passaging of papillomas or the potential to harvest virulent infectious viral particles to generate an infectious viral suspension. In this model it took 40 weeks to produce one graft site in which potentially infectious viral particles could be detected. In an improved animal model it would be desirable to markedly decrease the incubation time for inducing papillomas having infectious viral particles and more importantly to increase the success rate of papilloma formation evaluated by an increase in size and number of papillomas.

To date there are no animal models for human papillomavirus infections that are easy to generate, dependable, reliable and reproducible and which allow for serial passaging of papillomas and harvesting of infectious viral particles. There thus remains a need to develop an animal model in which a human papillomavirus can be easily propagated and serially passage without requiring complex surgical procedure, and which produces a great number of papillomas and infectious viral particles suspension.

The animal model of this invention is particularly useful for supporting the complete cycle of viral infection and vegetative growth, and, for selecting and testing candidate agents for the treatment or prevention of papillomavirus infections that would have physiological and pharmacological relevance in humans.

The model of the present invention produces highly reliable and reproducible papillomas from which infectious viral particles can be harvested. The animal model of this invention can further be used for screening and selecting candidate agents for the treatment or prevention of human papillomavirus infections and any conditions caused thereof.

It is a critical feature of the present invention, to provide a method for producing a xenograft animal model wherein injuring the host skin prior to grafting advantageously provides wound healing that fosters papilloma induction. It is a specific advantage of this invention to provide this injury by way of meshing, additionally providing stretching of the host skin to cover a larger graft area, thus reducing the demand for host skin tissue. Further, meshed engrafted tissue improves the survival and health of the engrafted skin tissue.

Therefore, it is a feature of the present invention, to provide a xenograft animal model, which may be used for the growth and propagation of papillomavirus. Particularly, these xenografted animals when infected with a papillomavirus form papillomas as an indication of papillomavirus infection. These animals are a superior model for induction of papillomavirus infection that is reliable and reproducible when compared with other known xenograft animal models.

It is a specific feature of the present invention, to provide human xenografted animals which may be used for the induction, growth and propagation of human papillomavirus, and from which infectious viral particles can be harvested thereby providing infectious viral stock suspension.

It is a further feature of the present invention, to provide such a viral stock suspension to be serially passaged to papillomavirus-free animals in order to induce papillomavirus infections in subsequent xenografted animals.

It is still another feature of the present invention to provide a method for the production of these xenografted animals in order to induce papillomavirus infections in these xenografted animals and in which papillomavirus can be harvested and propagated, and can be passaged to papilloma-free xenografted animals.

A further feature of the present invention is to provide a xenograft animal model to test potential therapeutic agents against papillomavirus infection.

The present description refers to a number of documents, the content of which is incorporated herein by reference.

SUMMARY OF THE INVENTION

Thus, the present invention is directed to a graft animal model for reproducible papilloma induction, and propagation of papillomavirus. This model serves also for screening and selecting a therapeutic agent against papillomavirus infection. The invention further provides a method for producing the grafted animal and the model thereby produced.

Therefore and in accordance with a first embodiment of the present invention there is provided a graft animal model for the induction and formation of papillomas, and for the propagation of human papillomavirus which is characterized by:

a recipient animal grafted with host skin tissue, said skin tissue having been injured prior to said grafting, inoculating said grafted skin tissue with an inoculum of a host-specific papillomavirus, wherein said grafted skin is supported by said recipient animal and is capable of inducing and sustaining growth of host-specific papillomavirus and harboring at least one papilloma containing infectious viral particles.

The success of the model of the present invention is based on the realization by the Applicant that the process of tissue healing following injury in the donor skin improves the tissue's susceptibility to PV infection and favors wart formation.

Within the model according to this first embodiment, there is comprised a recipient animal grafted with host skin tissue, wherein said skin tissue has been injured prior to said grafting, whereby said grafted skin is capable of inducing and sustaining growth of host-specific papillomavirus and harboring at least one papilloma containing infectious viral particles.

In accordance with a second embodiment of the present invention, there is provided a method for producing a graft animal model for propagating infectious papilloma viral particles, said method comprising the following steps:

obtaining skin tissue from a host donor and injuring said skin,
  grafting said injured skin tissue onto a recipient animal capable of accepting said skin tissue,
  inoculating said grafted tissue with an inoculum of a host-specific papillomavirus, and
  providing sufficient time for said papillomavirus to propagate in said grafted tissue and to form papillomas as an indication of papillomavirus infection.

An important aspect of this second embodiment is provided in the step of inducing tissue healing following injury in the host skin tissue to be grafted.

In a particular aspect of this second embodiment, inoculation of the injured donor skin tissue with a papillomavirus inoculum can be accomplished using for example papillomavirus suspension that can be applied either in-vitro or in-situ. Injured donor skin tissue inoculated in-vitro, pre-grafting can be engrafted cutaneously or subcutaneously onto the immuno-deficient recipient animal. Injured donor skin tissue that is engrafted cutaneously can also be inoculated in-situ post-grafting.

In a further aspect of the present embodiment, the subcutaneous papillomas formed in the infected grafted animal, can be exposed by cutting open the subcutaneous papillomas with an incision to the skin at the site of the subcutaneous papilloma growth. The exposed papilloma develops a morphology that is similar to cutaneous papilloma and can be observed and evaluated without having to anesthetize or kill the grafted animal.

In accordance with a third embodiment of the present invention, there is provided an graft animal model for screening candidate therapeutic agents for protecting, preventing or treating papillomavirus infection. Accordingly, a candidate agent (in a therapeutically effective amount and in admixture with a pharmaceutical carrier) is administered to the graft animal model of the present invention. The efficacy of the candidate agent is evaluated by means comprising; a change in size, growth and morphology of the papillomas, and/or a decrease in viral load and infectivity, when compared to a control papilloma from an untreated grafted animal.

Therefore, in accordance with a fourth embodiment of the present invention there is provided a method for evaluating the efficacy of a therapeutic agent useful against papilloma virus infection comprising the steps of:

providing a grafted animal model according to the present invention,
  inoculating said grafted host skin tissue with an inoculum of host-specific papilloma virus,
  treating said papillomavirus-infected animal by administering a candidate therapeutic agent in an appropriate pharmaceutical carrier, and
  evaluating the efficacy of said therapeutic agent in preventing the appearance, reducing the physiological symptoms or reducing the evidence of said infection in said infected animal.

Other objects, advantages and features of the present invention will become more apparent upon reading of the following non-restrictive description of the preferred embodiments with reference to the accompanying drawings which is exemplary and should not be interpreted as limiting the scope of the present invention.

BRIEF DESCRIPTION OF THE DRAWINGS

This patent or application file contains at least one drawing executed in color. Copies of this patent or patent application publication with color drawing(s) will be provided by the Office upon request and payment of the necessary fee.

Having thus generally described the invention, reference will now be made to the accompanying drawings, showing by way of illustration a preferred embodiment thereof, and in which: all figures represent a preferred embodiment of the invention consisting of a model of NIH-nu-bg-xid mice xenografted with meshed human foreskin tissue infected with low-risk HPVs.

Figure 1:
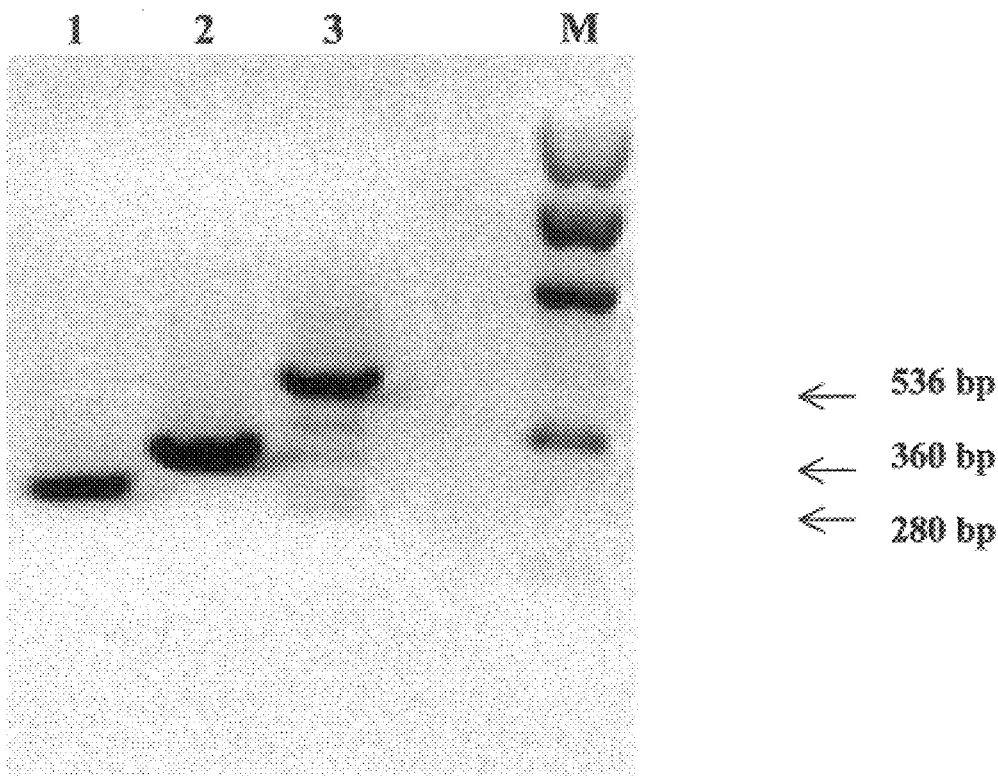
FIG. 1(A & B) shows the amplification products of DNA extracted from clinical samples of excised human papilloma tissue. These extracts were used as initial HPV stocks to induce first generation papillomas.
Figure 1:
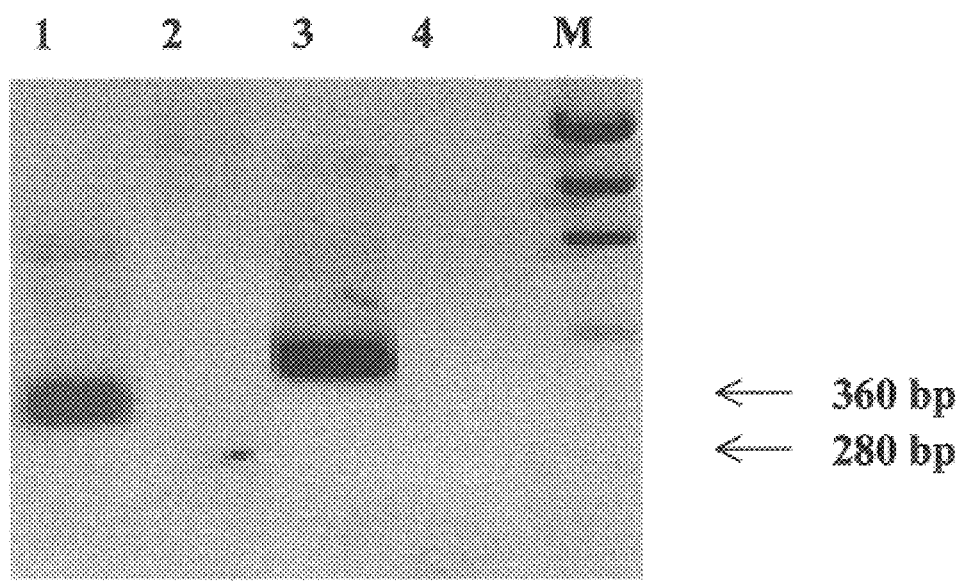

Panel A shows a mixture of HPV-6 and -11. In lane 1, primer pair VdB-6-U/D which comprise HPV-6 L2 open reading frame described by Mant et al. (1997, J. Virol. Meth. 66:169–178) amplified the expected 280 BP product. In lane 2, primer pair VdB-11 -U/D which comprise HPV-11 L1 open reading frame (Mant et al., supra) amplified the expected 360 bp product. In lane 3, a positive control, primer pair KM29/RS42 specific for human β-globin described by Saiki, in PCR Protocols (1990, Ed. Innis et al., pg: 13–20) amplified the expected 536 bp product. Lane M, represents a DNA molecular weight ladder. The arrows on the right indicate the molecular weights of the amplification products.

Panel B shows single type HPV-6 or -11 extracts. Using primer pair VdB-6U/D which comprise HPV-6 L2 open reading frame, the HPV-6 extract gave the expected 280 base pair product in lane 1, HPV-11 (lane 2) extract remained negative with the HPV-6 primer. When primer pair VdB-11 U/D which comprise HPV-11 L1 open reading frame, were used for PCR amplification, the expected 360 bp product was observed for HPV-11 extract (lane 3), but not for HPV-6 extract (lane 4).

Figure 2:
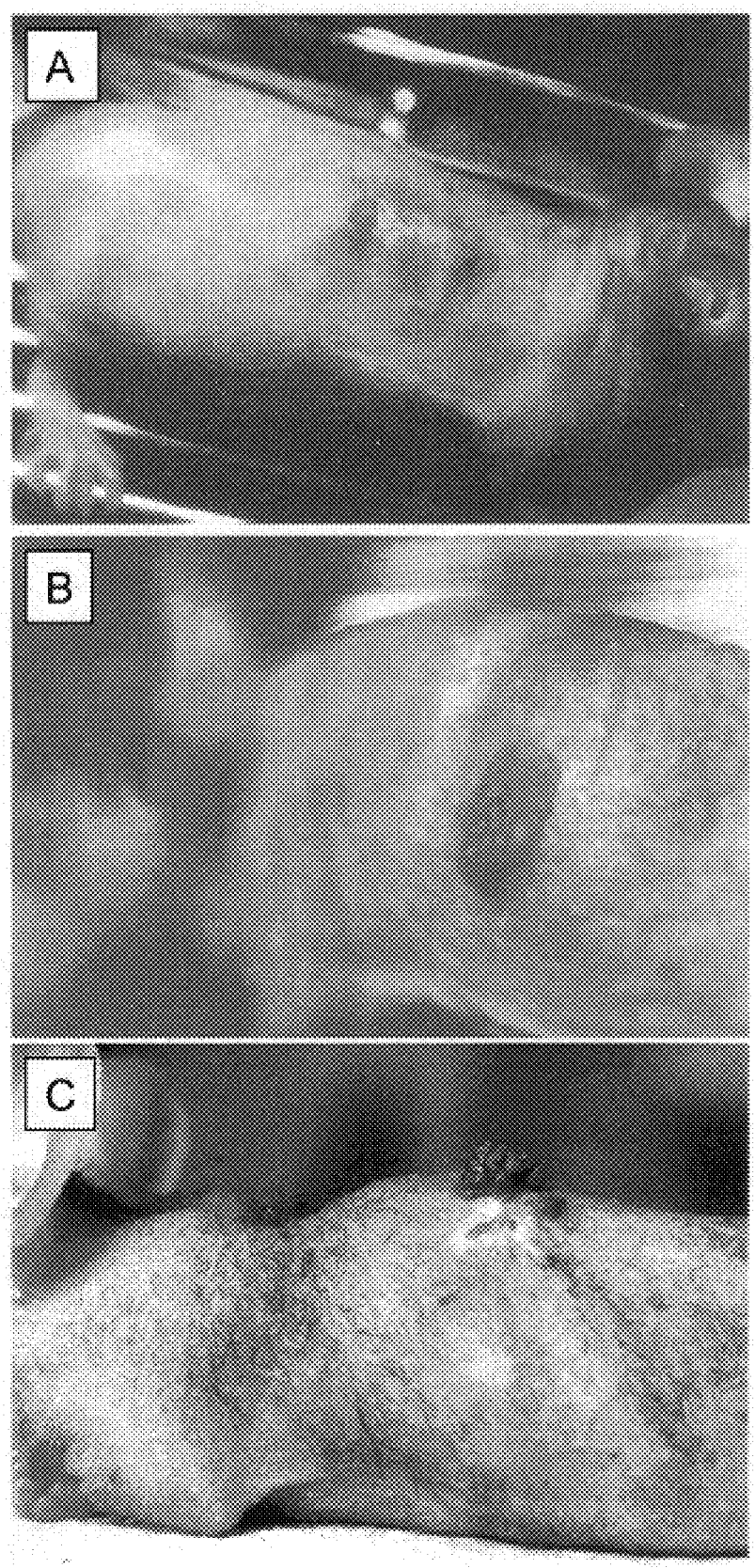

FIG. 2A shows the appearance of a site engrafted with human skin tissue injured by meshing that was not inoculated with human wart extract inoculum. There were no visible warts at the site.

FIG. 2B shows a first generation wart formed at the site engrafted with human skin tissue injured by meshing and inoculated with an inoculum containing both HPV-6 and -11 extracted from clinical samples of human wart tissue.

FIG. 2C shows a typical HPV wart induced by HPV-11 single type virus. A first generation wart formed at the site engrafted with human skin tissue injured by meshing and inoculated with an inoculum containing HPV-11 single-type extracted from clinical samples of human wart tissue.

Figure 3:
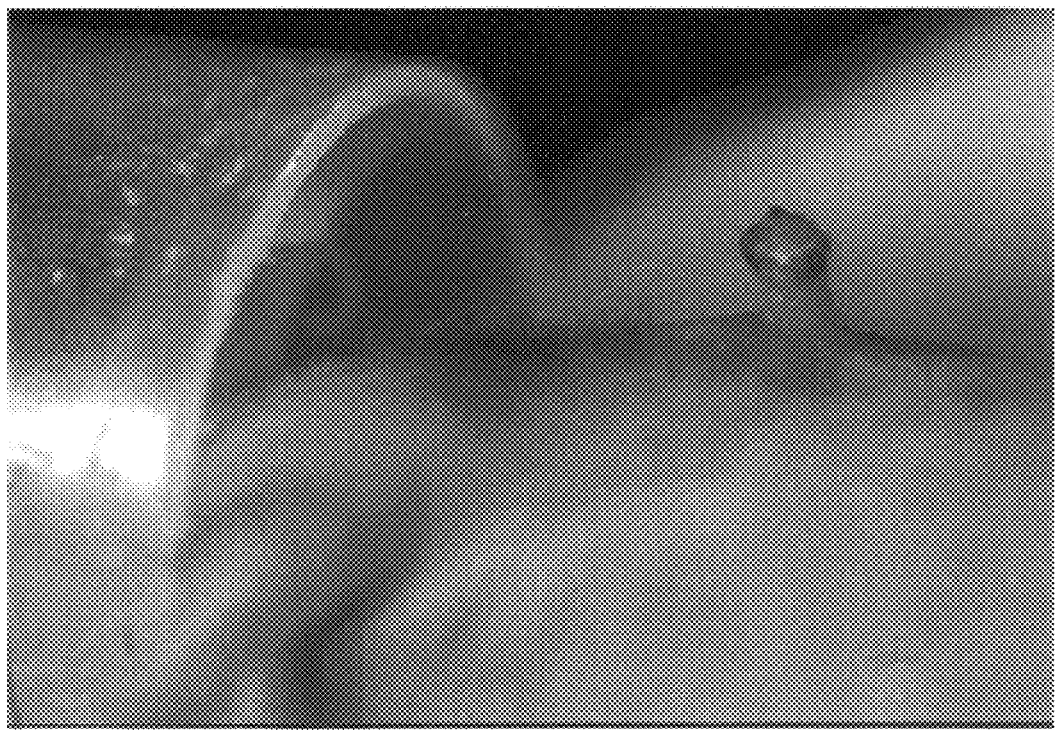

FIG. 3 shows an exposed subcutaneous papilloma. Human skin tissue was physically wounded by meshing, inoculated with an inoculum of human wart tissue extracted from clinical samples and engrafted subcutaneously. At about the 10$^{th}$ week post-grafting the skin covering the apex of the subcutaneous papilloma is cut with an incision, the skin is gently retracted and is fixed to the engrafted tissue using sutures, allowing the papillomas to grow outward and to protrude through the skin. These exposed subcutaneous papillomas develop a similar morphological and histological appearance as cutaneously growing papillomas.

Figure 4:
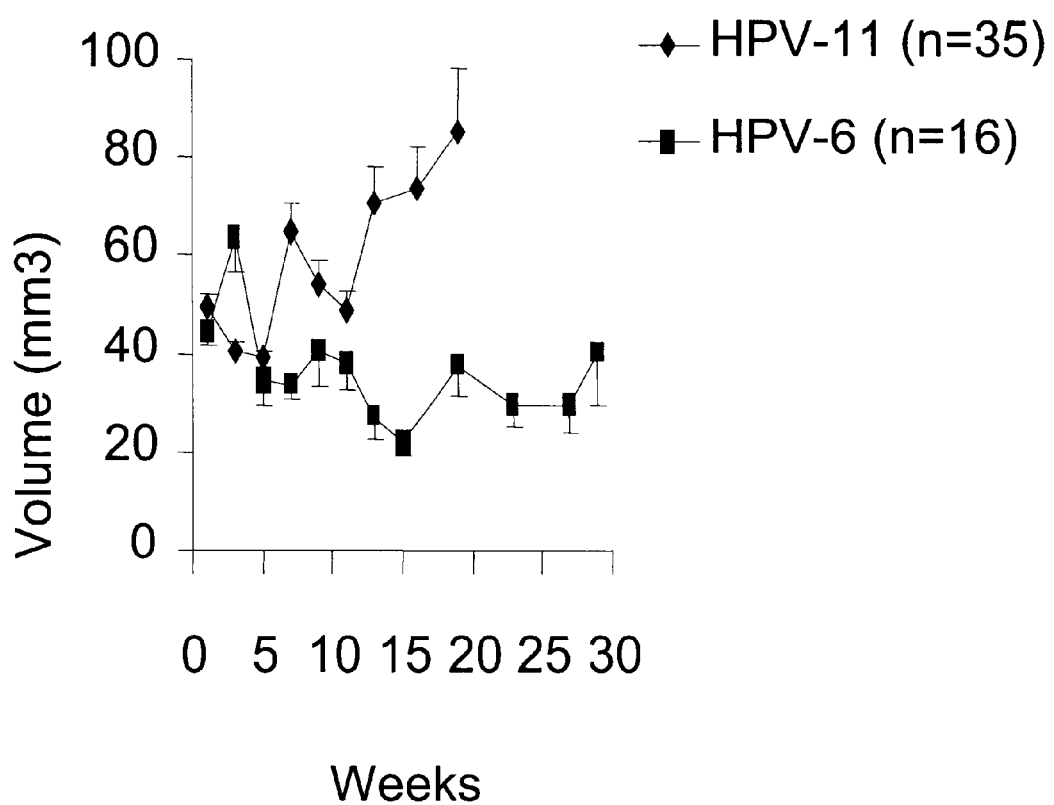
Figure 12:
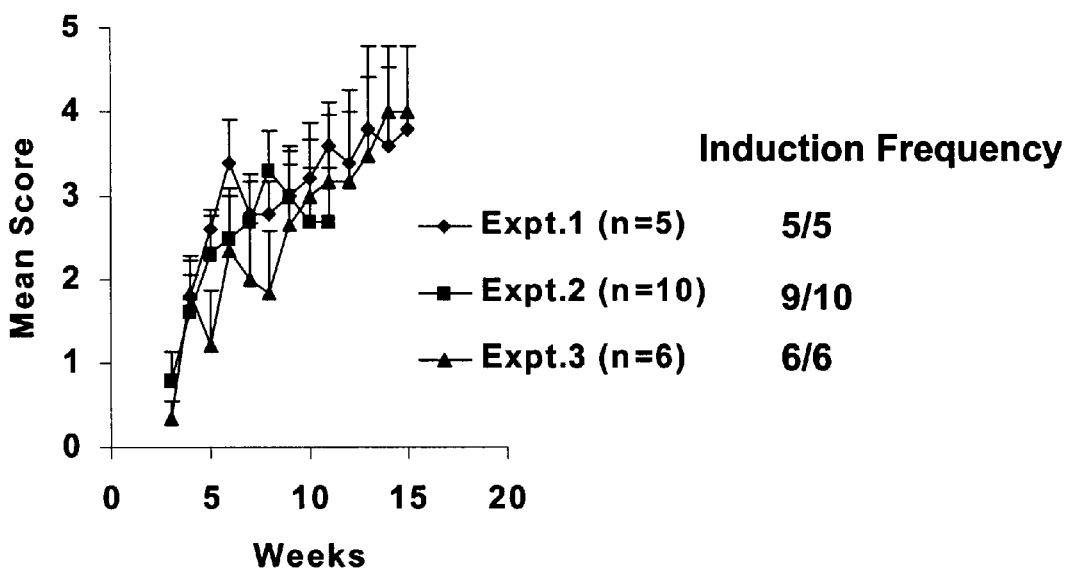
Figure 12:
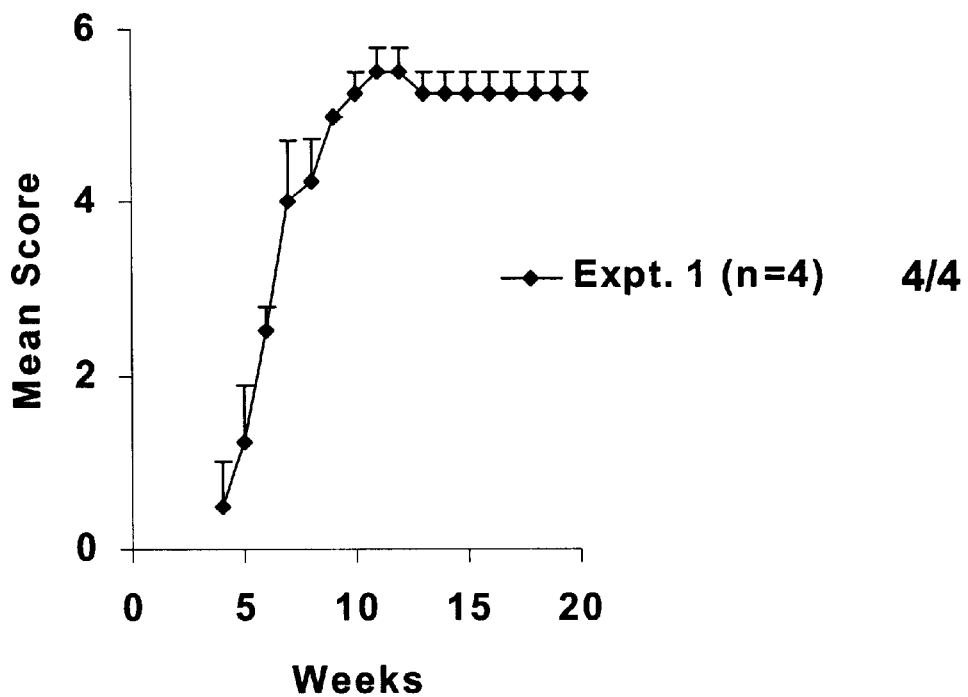
Figure 13:
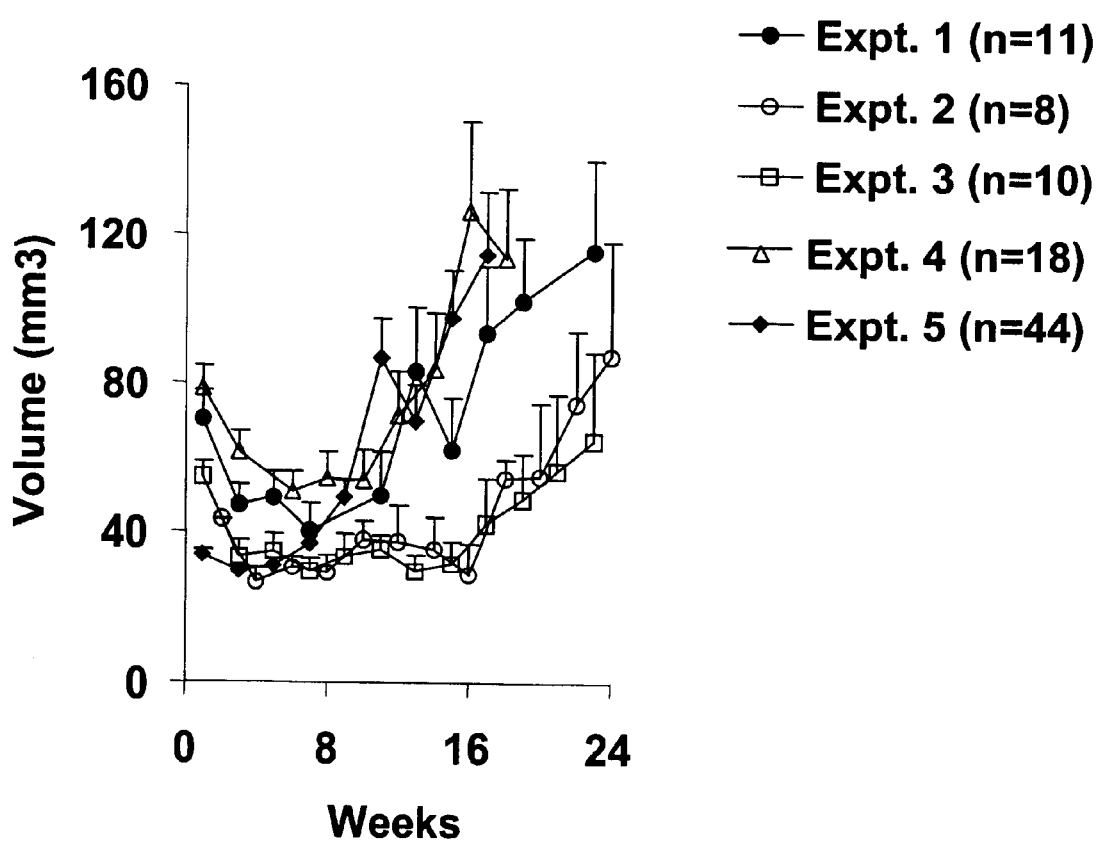

FIG. 4 shows the growth rate of first generation single type HPV-11 or -6 infected xenograft human foreskin tissues grafted sub-cutaneously. The volume was measured as the product of length×width×height. HPV-11 induced warts were collected at 20 weeks post-grafting for virus collection. Only a few HPV-6 infected grafts had moderate growth after 7 months. Successful single type HPV-11 or -6 infection and viral propagation were verified by PCR analysis (FIG. 9), typical histology, in situ hybridization, immunohistochemistry (FIG. 5), and infectivity of harvested virus in subsequent passages (FIGS. 12, 13).

Figure 5:
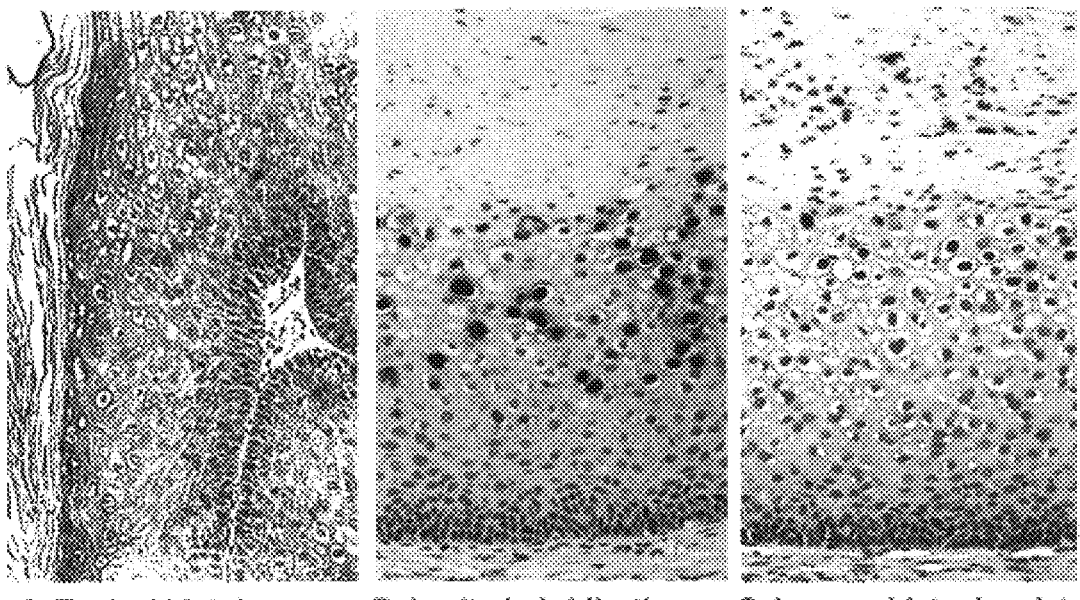

FIG. 5(A–C) shows a typical histology, in situ hybridization and immumohistology of HPV-induced xenograft warts.

Panel A. Wart tissues were fixed with formalin immediately upon collection. The samples were trimmed across epidermal to subcutis, desiccated, processed through xylene, and perfused with paraffin. Sections were cut at 5 μm, stained with hematoxylin and eosin for histology.

Panel B. For in situ hybridization, biotinylated DNA probes specific for HPV-6 or -11 were obtained from DAKO Corporation. Tissue sections were de-paraffined in xylene and re-hydrated through graded ethanol and water. Following protease digestion, probe solution was added to the slide. The slide were covered without sealing, and incubated for 6 min at 92° C. to denature HPV and probe DNA. Slides were then placed in a humid chamber for 1 hour at 37° C. Following hybridization, slides were subjected to a high stringency wash to reduce nonspecific hybridization. Specific hybridization was visualized by catalyzed reporter deposition using a tryamide signal amplification kit (GenPoint, DAKO Corporation), brown intracellular staining was identified as positive signals.

Panel C. For immunohistochemistry study, murine IgG1 monoclonal antibody (Novocastra Laboratories Ltd, UK) directed against HPV-6 L1 coat fusion protein (amino acids 40–233) common to HPV types 6, 11, and 18, was used to detect HPV-6 or -11 L1 expression in the wart tissues. Biotinylated goat anti-mouse IgG1 was added to react with the antibody followed by immunoperoxidase staining which labels positive cells in brown.

Figure 6:
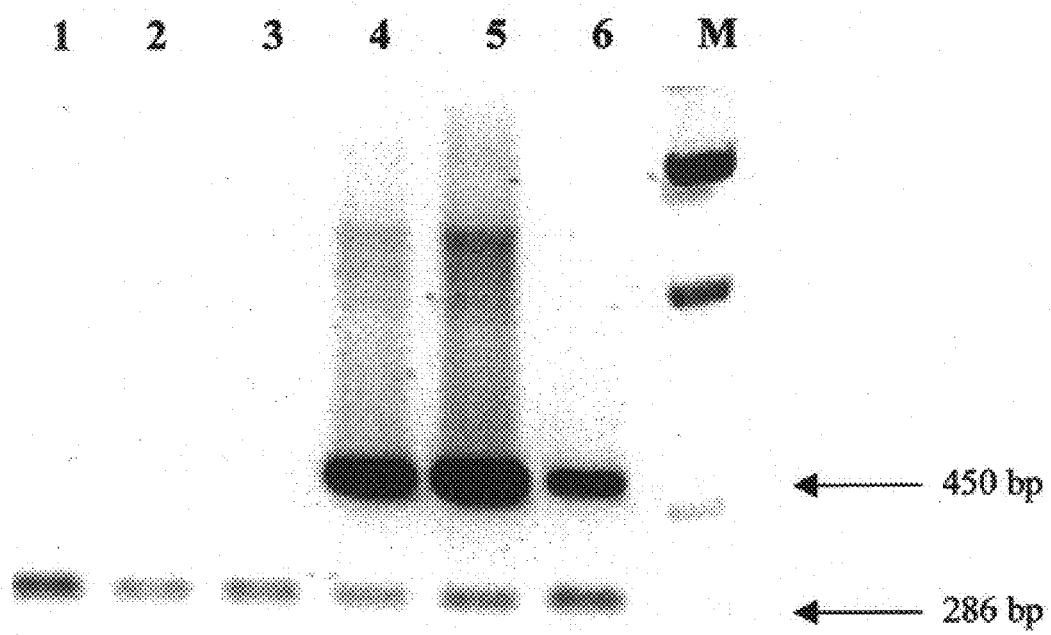

FIG. 6 demonstrates the presence of HPV DNA extracted from swab samples of 1$^{st}$ generation papillomas induced by a mixture of HPV-6 and-11. DNA was extracted from swab samples taken from sites engrafted with: non-inoculated meshed human skin tissue (lanes 1–3), and meshed and inoculated human foreskin tissue (lanes 4–6). The DNA from these swabs was extracted and digested with Hind III. An aliquot of the digested DNA was co-amplified with the following primer pairs: MY09/MY011 which amplify the ORF region of the L1 gene in HPVs non-specifically, and S-GH20/SPCO04 which amplify a region in the human β-globin gene (primer sequences are as described in Mant et al., supra). The amplification products of the DNA derived from 1$^{st}$ generation wart tissue show the expected 450 bp and 286 bp bands corresponding to HPV L1 gene and β-globin DNA, respectively.

Figure 7:
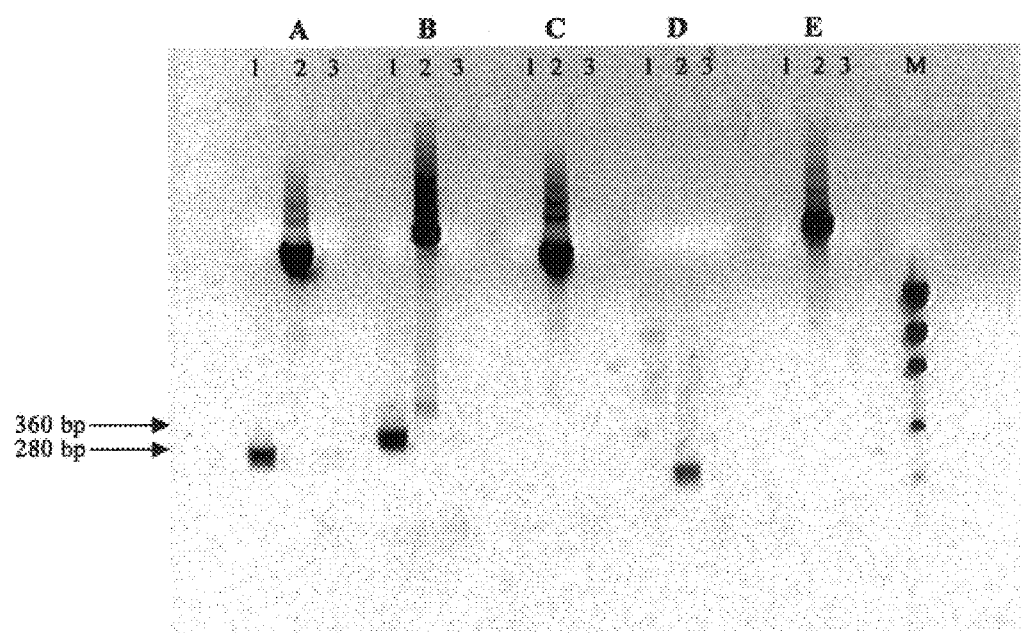

FIG. 7 shows the results of the amplification products of DNA isolated from 1$^{st}$ generation cutaneous wart tissue induced by a mixture of HPV-6 and -11. The isolated DNA was amplified with HPV type specific primers as described in Mant et al. (supra). The lanes in group A, B, C, D, and E correspond to the amplification products of primers specific for HPV-6, -11, -16, -18, and -31, respectively. In each group, lane 1 corresponds to the amplification product of DNA extracted from 1$^{st}$ generation cutaneous wart tissue, lane 2 corresponds to a positive control and lane 3 to a negative control (no DNA in the amplification reaction). The positive controls are standard HPV plasmids pUC19-HPV6, pBR322-HPV11, pBluescript-HPV16, pBR322-HPV18 and pBR322-HPV31 containing HPV-6, -11, -16, -18 and -31 DNA, respectively, obtained from American Type Culture Collection (Manassas, Va., U.S.A.). Amplification of these plasmids produces amplification products greater than 3 Kb for the control plasmids of HPV-6, -11, -16 and -31. Lane M represents the molecular weight ladder. The amplification products demonstrated the presence of HPV-6 (lane A1) and 11 (lane B1) in the $_1$st generation cutaneous papillomas, but not the high risk types HPV-16, -18, and -31.

Figure 8:
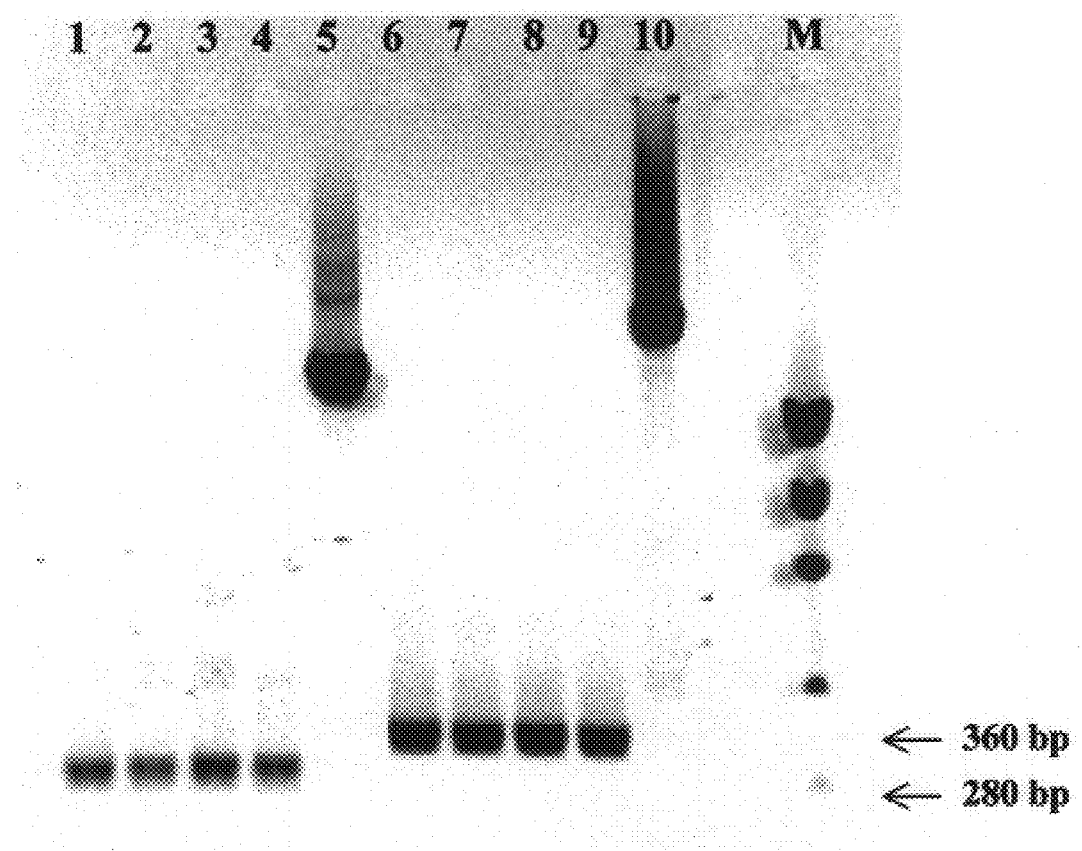

FIG. 8 shows the presence of HPV types 6 and 11 in subcutaneously engrafted sites infected with a mixture of HPV-6 and -11. DNA isolated from swab samples obtained from the surface of four distinct 1$^{st}$ generation exposed subcutaneous papillomas are analyzed by amplification. Specific primers to HPV types 6 and 11 confirm the presence of HPV-6 (lanes 1 to 4) and HPV-11 (lanes 6 to 9). Lanes 5 and 10 are positive controls as described in FIG. 7.

Figure 9:
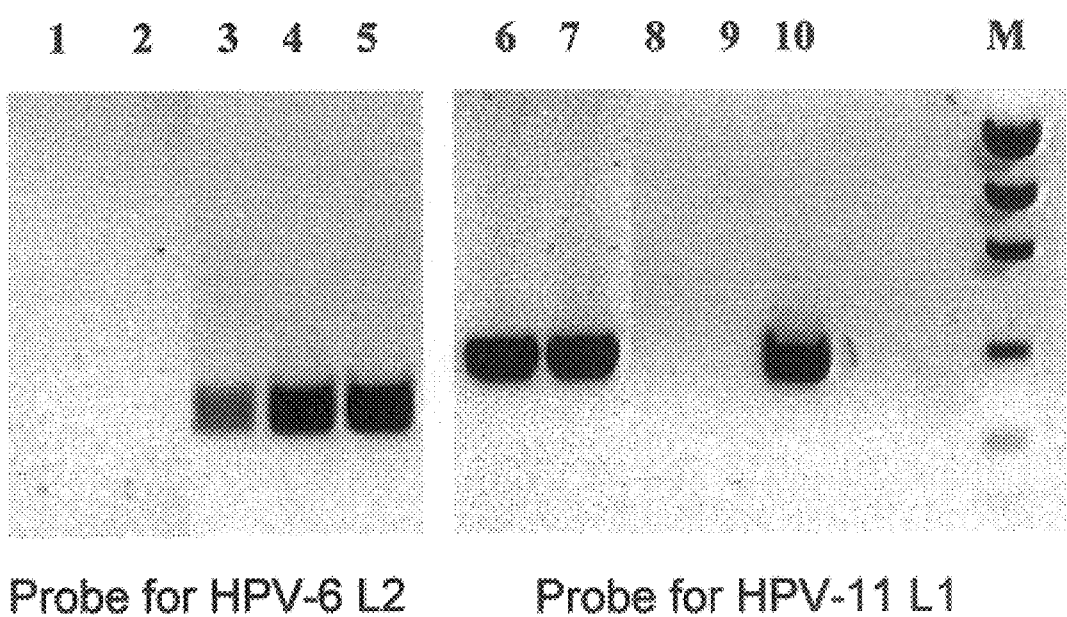

FIG. 9 represents a PCR analysis of single type HPV-6 or -11 induced xenograft warts. Primer pair VdB-6U/D which comprise HPV-6 L2 open reading frame amplified the expected 280 bp products from both HPV-6 induced subcutaneous warts (lanes 3 and 4), similar to that obtained with control plasmid pU19-HPV-6 (lane 5). In contrast, HPV-11 warts did not have positive signals when probed for HPV-6 (lanes 1 and 2). In lanes 6 and 7, primer pair VdB-11 U/D which comprise HPV 11 L1 open reading frame amplified the expected 360 bp products from both HPV-11 induced cutaneous and subcutaneous warts, similar to that observed with control plasmid pUC19-HPV-11 (lane 10). HPV-6 warts gave negative signal when probed for HPV-11 (lanes 8, 9).

Figure 10:

FIG. 10 shows the morphology at 9 weeks post-grafting of a 2$^{nd}$ generation cutaneous papilloma passaged from a 1$^{st}$ generation papilloma induced with mixed-type HPV-6 and -11.

Figure 11:
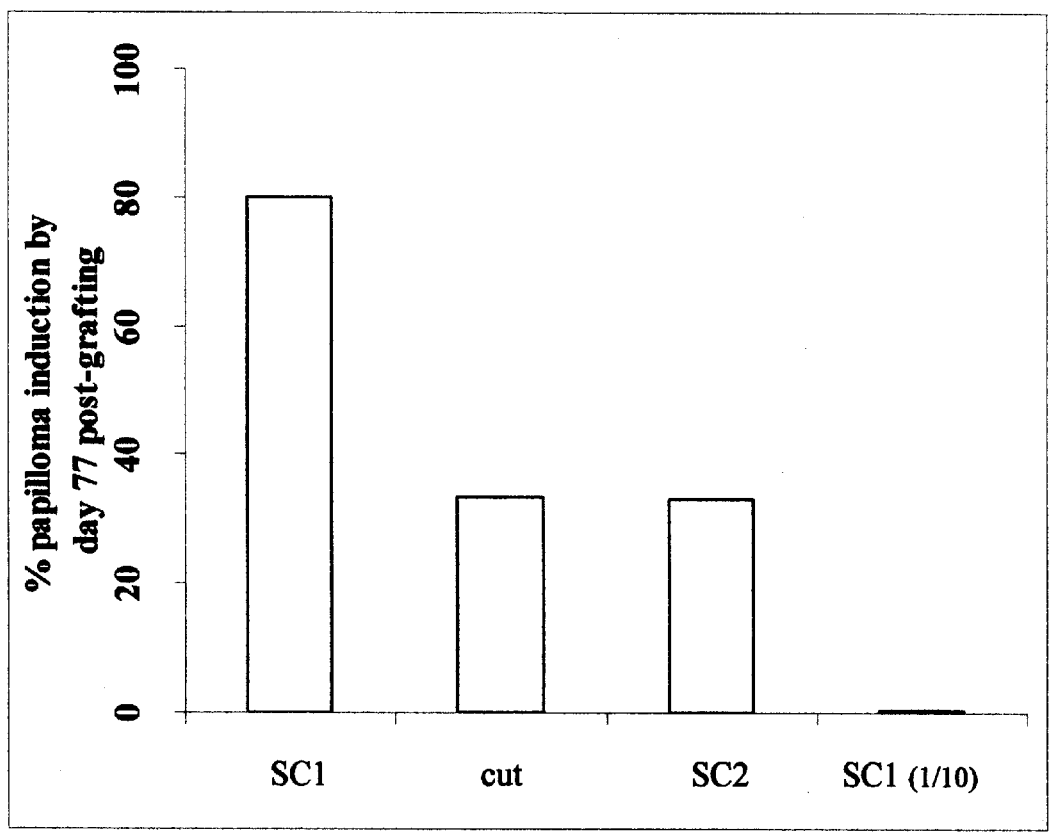

FIG. 11 summarizes of the % wart induction in the cutaneous model (day 77 post-grafting), in 2$^{nd}$ generation xenografted animals inoculated with HPV harvested from 1$^{st}$ generation papillomas induced with mixed-type HPV-6 and -11. Subcutaneous papillomas were subjected to two sequential viral particle extractions, viral stock from the first extraction (SC1) and second extraction (SC2) induced 80% (8 out of 10 engrafted sites) and 33% (1 out of 3 engrafted sites) papillomas, respectively. A 1:10 dilution of SC1 did not induce any papillomas (0 out of 5 engrafted sites). Viral particles harvested from cutaneous (cut) papillomas induced 33% (2 out of 6 engrafted sites) papillomas in the 2$^{nd}$ generation animals. This result suggested that viral stock extracted from subcutaneous warts may be more effective in generating infectious particles for subsequent infections.

FIG. 12(A & B) shows single type HPV-11 wart induction in the cutaneous model by viral stock originally generated from sub-cutaneous xenograft warts.

Panel A shows 3 individual experiments with highly reproducible papilloma induction frequency and growth rate in the 2$^{nd}$ generation.

Panel B shows that the 3$^{rd}$ passage papilloma induction is highly reproducible. Papilloma induction, passage and scoring criteria were as described in the text.

FIG. 13 shows subcutaneous growth of single type HPV-11 infected xenograft in the 2$^{nd}$ and 3$^{rd}$ generation.

Panel A. Experiments 1 to 4 show 4 individual experiment in the 2nd generation.

Panel B. Experiment 5 shows a 3$^{rd}$ passage in the subcutaneous model. Papilloma induction, passage and volume measurement was as described in the text.

Figure 14:
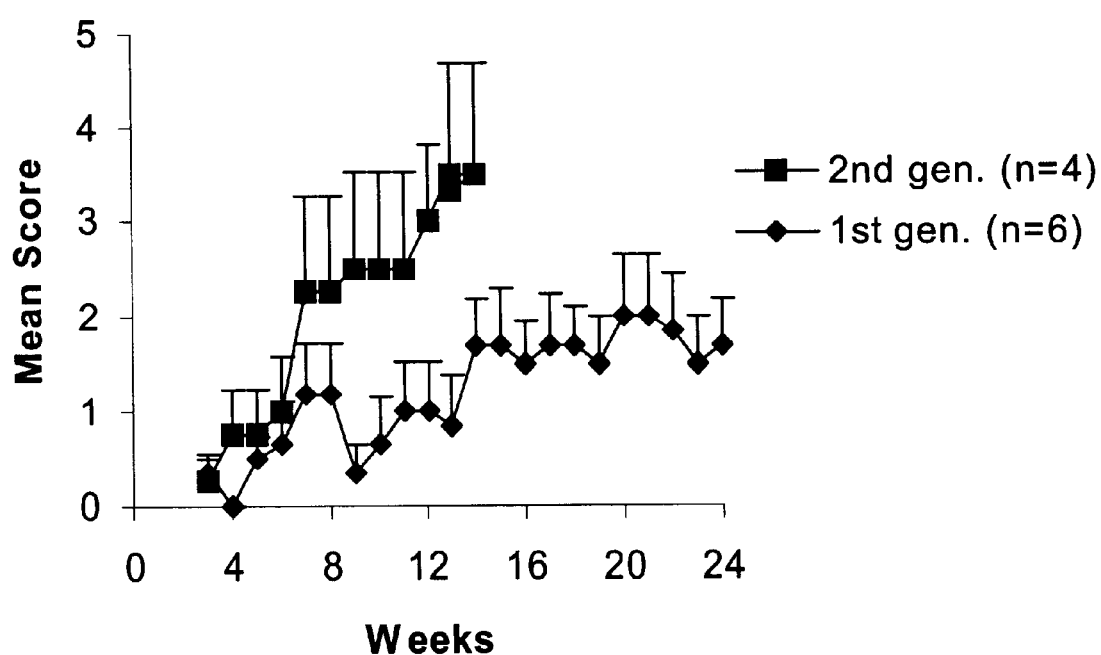

FIG. 14 shows comparative growth rates of 1$^{st}$ and 2$^{nd}$ generation warts induced by single type HPV-6 in the cutaneous model. The 2$^{nd}$ generation warts were induced by a small stock prepared from 24 small sub-cutaneous and 1 small cutaneous 1$^{st}$ generation warts collected s described in FIG. 4. Cutaneous wart scoring was as described in the text.

DETAILED DESCRIPTION OF THE PREFERRED EMBODIMENTS

Definitions

Unless defined otherwise, the scientific and technological terms and nomenclature used herein have the same meaning as commonly understood by a mammal of ordinary skill to which this invention pertains. Generally, the procedures for cell culture, infection, molecular biology methods and the like are common methods used in the art. Such standard techniques can be found in reference manuals such as for example Sambrook et al. (1989, Molecular Cloning—A Laboratory Manual, Cold Spring Harbor Laboratories) and Ausubel et al. (1994, Current Protocols in Molecular Biology, Wiley, N.Y.).

"Sequence amplification" is a method for generating large amounts of a target sequence. In general, one or more amplification primers are annealed to a nucleic acid sequence. Using appropriate enzymes, sequences found adjacent to, or in between the primers are amplified. An amplification method used herein is the polymerase chain reaction (PCR).

"Amplification primer" refers to an oligonucleotide capable of annealing to a DNA region adjacent to a target sequence and serving as the initiation primer for DNA synthesis under suitable conditions well known in the art. The synthesized primer extension product is complementary to the target sequence.

"Grafted animal" is a recipient animal onto which is grafted a graft tissue.

"Allograft" is the engrafting of tissue obtained from a donor animal onto a recipient animal that is of the same species.

"Xenograft" is the engrafting of tissue obtained from a donor animal onto a recipient animal that is a different species from the donor animal.

"Xenograft animal" is a recipient animal onto which is grafted a xenograft.

The terms "papilloma" and/or "warts" are used interchangeably herein and define a highly proliferative tissue growth caused by papillomavirus infections. These have gross anatomical and histological features well known in the art and occur cutaneously and subcutaneously.

The term "in-situ" refers to inoculating a living animal. That is, an inoculum is applied to a living animal by any means well known in the art. Specifically and for use herein, the term describes inoculating donor tissue after engrafting onto a recipient animal. It will be understood that in situ inoculation is preferably performed on a cutaneous graft.

"Passaging" refers to collecting papillomavirus from a previous generation of grafted warts from an infected-graft donor animal and inducing warts to a recipient animal that is apparently free of papillomavirus infection. The recipient animal can be selected from a group consisting of immuno-compromised animals or a natural host to the papillomavirus. The animal receiving the passaged papillomavirus is referred to herein as a "subsequent animal" or a "subsequent recipient animal". A preferred means of passaging the virus consist in infecting meshed graft tissue prior to its grafting onto the subsequent recipient animal.

The term "injuring" refers to any means of causing profound injury or wound to a tissue, which would result in tissue healing activity. Tissue injury can be induced by physical wounding or chemical damage. Non-limiting examples of physical wounding include: perforating, slitting, cutting, punching holes, burning and meshing using appropriate tools known in the art (e.g. scalpels, needles, pins, hole borers, meshers, etc.). Non-limiting examples of chemical damage include; enzymatic treatment and chemical burning. Tissue healing activity comprises new cell growth and increases in cellular growth factors and adhesion factors such as kinins and integrins. In addition, tissue healing activity may also be induced by other means such as electrical and chemical stimulation, chemical stimulation may include application of growth factors and/or enzymes to the tissue.

The term "meshing" refers to a means of treating tissue, specifically skin tissue whereby small openings or holes are poked throughout the tissue. Meshing can be accomplished manually or by use of a machine designed for this purpose. Meshing (Pope et al., 1990, 20:177–187), is a procedure mostly used for medical and veterinary applications to expand graft skin tissue to encompass greater surface area to cover large skin wounds. Rob et al. (Journal of Burn Care and Rehabilitation, 1987, 8(5):371–375), describe an animal model in which meshed human skin is grafted onto nude mice to investigate problems of scarring in the allografting of severely burned patients. The failure to generate a human xenograft model for propagating HPV has prompted Applicant to attempt the procedure of meshing human skin to generate a human xenograft model. This is the first time this technique is applied for the purpose of producing a graft model for use in propagating a fastidious organism causing viral infections.

Preferred Embodiments

Recipient Animal

In a particular aspect of this invention, the recipient animal is a non-human mammal capable of receiving and supporting a graft. Particularly, the recipient animal is capable of receiving a xenograft by being immuno-compromised and is mostly incapable of mounting a graft-rejection immune response thereby accepting the foreign tissue as self. Preferably, the recipient animal is immuno-compromised either by being immuno-deficient or immuno-suppressed by biological or chemical means. Such biological or chemical means include immuno-suppression by repeated treatment with cyclosporin or other immuno-suppressive agents well known in the art. More preferably, the immuno-compromised animal is immuno-deficient. The term immuno-deficient is used to describe a recipient animal in which the immune system has been partly or completely compromised in order to allow engrafted foreign cells or tissue to grow with minimal chance of rejection by the recipient animal.

Even more preferably, the non-human mammal is a rodent, more preferably a mouse, rat, rabbit, guinea-pig, or hamster. More particularly, this mammal is a rodent such as a rat or a mouse having no functional T-cell immunity, non-limiting examples being severe combined immuno deficient (SCID) mice, SCID/beige mice, nude mice, or NIH-nu-bg-xid mice. Specifically the recipient animal has no or little functional T-cell immunity or B cells or NK cells. Most preferably, the recipient animal is hairless to facilitate grafting procedures such as the NIH-nu-bg-xid mouse.

Donor Tissue/animal

In a further aspect of the present invention, the donor tissue can be taken from any animal that is a natural host to papillomavirus. These animals are listed in Olson, C. (1987, The Papaviridae, volume 2, pages 39–66). Non-limiting examples of a donor animal can be selected from: dog, cattle, horse, swine, rabbit (cottontail, domestic and New-Zealand White (NZW)), deer, non-human primates and humans. These donor animals are hosts to the corresponding papillomavirus such as: canine oral papillomavirus, bovine papillomavirus, equine papilloma virus, swine papillomavirus, cottontail rabbit papillomavirus (CRPV), deer fibroma virus, primate papillomavirus and human papillomavirus (HPV), respectively. In a preferred aspect of this invention, the donor animal is human. In a preferred aspect of this invention the human tissue is foreskin tissue obtained from infant circumcision from a medical clinic or hospital.

Allografting or Xenografting

In a particular embodiment of the present invention, there is provided a model for grafting tissue from a donor animal that is the same species (allograft) or of foreign species (xenograft). As stated above, when the graft is foreign (xenograft) the recipient animal must be immunocompromised to be able to support such graft without rejecting it as non-self.

Therefore, in a preferred embodiment of the invention there is provided a xenograft animal model capable of forming human papillomavirus infection. The model is reliable and easily reproduced, and is particularly useful for the induction and formation of demonstrable human papillomas. More particularly, the xenograft animal model is useful for the propagation of human papillomavirus and the harvesting of infectious viral particles of HPV low-risk and high-risk.

Graft Tissue Injury

The success of the model of the present invention is based on the realization that profound tissue injury of skin obtained from donors is important in the induction of human papillomavirus infection in the graft model. Preferably, there is provided the means for injuring skin tissue for use in generating a graft animal model having increased susceptibility to PV infection. In an important aspect of this invention, the induction of tissue healing in the grafted tissue is as a consequence of tissue injury. Tissue injury can be achieved using physical wounding and chemical damage. Physical wounding can be achieved with slitting, cutting, burning, perforating, poking holes, meshing, etc. by using any tools known in the art such as needles, scalpels, forceps, pins, hole punchers, meshing machine, etc. Chemical damage may comprise enzymatic treatment. More preferably, the induction of tissue healing as a consequence of injury is particularly due to physical wounding and most preferably meshing. Physical wounding enhanced the success rate in initiating infection by a fastidious organism, specifically human PV in the xenograft human animal model. The success of physical wounding, particularly meshing in improving the induction of human papillomas may be attributed to several mechanisms. Wounding, particularly meshing may stimulate neoepithelization (Harries et al. 1995, Aust NZ J Surg, 65:600–603) thus increasing the population of basal cells which are the target cells for HPV. Further, tissue wounded by meshing may lead to pronounced healing process. During this healing process, integrins such as $\alpha 6 \beta 4$, become widely expressed. A recent study (Evander et al. 1997, J. Virol 71:2449) suggests that integrin $\alpha 6 \beta 4$, may be a receptor for papillomavirus binding and entry into the host cells. Therefore, healing of human skin tissue after physical wounding appears to be an important factor in the development of graft model for PV infection.

Therefore, in a preferred embodiment of this invention, human skin tissue for xenografting is physically wounded and inoculated with a HPV inoculum. The Applicant reproducibly induced demonstrable cutaneous and subcutaneous papillomas by meshing the skin prior to grafting. Parallel experiments without skin meshing, using the same viral stock failed to induce papillomas in cutaneously and subcutaneously engrafted tissue.

Therefore in a preferable aspect of the invention, the physical wounding of human skin tissue is accomplished by meshing, either manually or with the use of a meshing machine. More preferably, meshing of the skin tissue is accomplished with the use of a meshing machine. Meshing advantageously provides stretching human skin to cover a larger graft area, thus reducing the demand for human skin tissue. Further, meshing of the engrafted tissue facilitates the transudation of extrudates, thus improving the survival and health of the engrafted skin tissue (Pope et al., supra).

Inoculum

In an additional preferred aspect of the invention, the human papillomavirus used for preparing the inoculum is selected from HPV low risk or high risk type. Low risk type consisting of types 6, 11 and 13. High risk types consisting of types 16, 18, 35, 45, 52 and 58. Preferably the papillomavirus is low risk consisting of types 6, 11 and 13.

In a particular aspect, the initial HPV inoculum is derived from clinically excised human papillomas obtained from a medical clinic. The viral particles obtained from these clinical samples comprise a mixture of HPV types including 6 and 11, or single type HPV-6 or -11. Therefore, the xenografted human skin tissue is inoculated with a mixed inoculum comprising HPV types 6 and 11, or single type HPV-6 or -11.

In an additional aspect of the invention, there is provided a viral suspension that is infectious to human skin tissue, specifically xenografted human skin tissue. Advantageously, the viral suspension can therefore be passaged to the animal model of the present invention for generating subsequent HPV xenograft animals. Preferably, the viral suspension harvested from the human xenograft animal model of the present invention can be used to isolate a viral suspension containing either single type or mixture of HPV types. Most preferably, the viral suspension contains a single viral type.

Advantageously, a pure viral isolate is useful for genotypic and phenotypic characterization of pure HPV types. On the other side, the infection with mixed types would allow to address questions related to viral type predominance and interactions.

Inoculation

The term "inoculation" refers to a means for introducing infectious virus, virions or viral particles to a non-infected tissue. The inoculum can be a clinical sample, a suspension which is derived from a clinical sample or cultured sample, or an isolated strain. The inoculum can be comprised of a single pure viral strain or type, or a mixture of more than one viral strain or type.

In a particular aspect of inoculation, the donor skin tissue is scarified prior to or during inoculation. Scarification of the donor skin tissue can be accomplished using an instrument for wounding the tissue, such as a knife, scalpel, needle, etc. Preferably the instrument used for scarification is dipped in a papillomavirus suspension thereby inoculating papillomavirus particles at the same time as scarifying the skin tissue (in-vitro, pre-grafting). This pre-grafting inoculation (in-vitro) may also be accomplished by means such as soaking the scarified tissue in a papillomavirus suspension or by overlaying the pre-grafted tissue with a viral suspension.

In an alternative aspect of the invention, the scarified skin tissue is later inoculated with a papillomavirus suspension, in-situ immediately post-grafting; or, in-situ a few weeks post-grafting. This post-grafting inoculation (in-situ) may also be accomplished by overlaying the grafted tissue with a viral suspension, or by injecting the grafted tissue with a viral suspension or a combination thereof.

Cutaneous or Subcutaneous Grafting

In an additional aspect of the present invention the graft tissue is inserted subcutaneously and/or cutaneously onto the recipient animal. In the cutaneously grafted tissue the papillomas are formed on the surface of the xenografted human tissue. In the subcutaneously xenografted tissue the papillomas are formed subcutaneously at the site of the grafted human tissue. Thus, the present invention provides human xenografted animal models capable of having demonstrable cutaneous and subcutaneous papillomas.

Exposing the Wart

In a preferred aspect, the subcutaneous papillomas can be exposed and allowed to develop into cutaneous papillomas. Accordingly, the subcutaneous papillomas can be exposed by any means known in the art and allowed to develop into cutaneous papillomas. In a non-limiting example, the skin covering the apex of the subcutaneous papilloma is cut with an incision, the skin is gently retracted and held back allowing the papilloma to grow outwardly and protrude through the skin. These exposed subcutaneous papillomas develop similar morphological and histological appearance as cutaneous papillomas. Preferably the cut skin is held back by suturing the host skin to the grafted tissue.

Harvesting

In a further aspect of this invention, HPV can be extracted from the infected tissue of the xenografted animal model of this invention, thus providing a viral suspension. Particularly, papilloma tissue obtained from the xenografted animal model of the present invention provide infectious particles to be comprised in a viral suspension. The virions are harvested from the papilloma tissue by means well known to a mammal skilled in the art. In a non-limiting example, the excised papilloma tissue is homogenized in an appropriate homogenizing buffer that is known in the art and centrifuged. The supernatant comprising the virions is collected either for immediate use or stored for later use. Preferably the viral suspension is stored in phosphate buffered saline supplemented with antibiotics.

Screening Therapeutic Agents

In a preferred embodiment of the present invention, there is provided an animal model for screening candidate therapeutic agents against human papillomavirus. Particularly, the animal model has been demonstrated to be highly reproducible and "propagatable" from generation to generation providing visible human papillomas and infectious viral particles as an indication of human papillomavirus infection. Preferably, the candidate agent in a therapeutically effective amount and in admixture with a pharmaceutical carrier, is administered to the animal model of the present invention. The therapeutic agent is selected for the purpose of antagonizing human papillomavirus infection including; protecting, preventing and treating human papillomavirus infection in an individual in need of such medication. The therapeutic agent may be used singly or in combination with other means for intervening in HPV infection. Particularly, the therapeutic candidate agent is a compound capable of preventing the progression of human papillomavirus infection in an individual. Most preferably, the therapeutic candidate agent is a compound capable of eliminating a human papillomavirus infection or a recurrence thereof in an individual.

Alternatively, the therapeutic candidate agent is a compound capable of eliciting an immune reaction in a mammal against human papillomavirus infection thereby providing immunizing agents against papillomavirus infections. Potential immunizing agents are administered in a therapeutically effective amount and with any suitable carrier, with the purpose of eliciting antibodies against human papillomavirus. Such agents may provide partial or complete immunity in an individual.

In a particular aspect of this embodiment, the therapeutic candidate agent is administered to the animal model of the present invention and to an individual in need by any means known in the art including topical, oral or systemic.

Accordingly, the means to administer such an agent/s to an animal includes oral, topical or systemic, in a vehicle comprising one or more pharmaceutically acceptable carriers, the proportion of which is determined by the solubility and chemical nature of the compound, chosen route of administration and standard biological practice.

For oral administration, the agent/s or a therapeutically acceptable salt thereof can be formulated in unit dosage forms such as capsules or tablets each containing a predetermined amount of the active ingredient, in a pharmaceutically acceptable carrier. For oral administration, the compound or a therapeutically acceptable salt is administered in accordance with the body weight of an animal per day, in order to achieve effective results.

For topical administration, the agent/s can be formulated in pharmaceutically accepted vehicles containing the active agent/s. Such formulations can be in the form of a solution, cream or lotion. With reference to topical application, the agent/s is administered topically in a suitable formulation to the infected area of the body such as skin and genitalia in an amount sufficient to cover the infected area. The treatment should be repeated, for example, every four to six hours until lesions heal.

For parenteral administration, the agent/s may be administered either intravenously, subcutaneous or intramuscular injection, in compositions with pharmaceutically acceptable vehicles or carriers. For administration by injection, it is preferred to use the agent/s in solution in a sterile aqueous vehicle which may also contain other solutes such as buffers or preservatives as well as sufficient quantities of pharmaceutically acceptable salts or of glucose to make the solution isotonic. With reference to systemic administration, the agent/s is administered at a dosage in accordance with the body weight of an animal or individual per day in order to achieve effective results. Although the selected agents comprised in the formulations disclosed hereinabove may be effective and relatively safe medications for treating papilloma viral infections, the possible concurrent administration of these formulations with other treatments against papilloma virus infections are also included. These treatments include the use of cytotoxic agents such as, trichloroacetic acid, podofilox and podophyllin; immunotherapy agents such as, interferon and imiquinod, and, physical methods such as, electrosurgery, cryotherapy, excision surgery and $CO_2$ laser.

Suitable vehicles or carriers for the above noted formulations are described in standard pharmaceutical texts, e.g. in Remington's "The Science and Practice of Pharmacy", 19th ed., Mack Publishing Company, Easton, Penn., 1995, or in "Pharmaceutical Dosage Forms And Drugs Delivery Systems", 6th ed., H. C. Ansel et al., Eds., Williams & Wilkins, Baltimore, Md., 1995.

The dosage of the agent/s will vary with the form of administration and the particular active agent/s chosen. In general, the agent/s is most desirably administered at a concentration level that will generally afford antiviral effective results without causing any harmful or deleterious side effects to the animal.

The efficacy of the candidate agent can be determined by means including: effectiveness of the agent on the papillomas' size and growth, viral load and infectivity of viral particles, and other molecular and cellular parameters such as histology, in situ hybridization, PCR and immunohistochemistry.

EXAMPLES

Materials and Methods

The immuno-deficient animals, NIH-nu-bg-xid mice were purchased from Charles River Laboratories; Wilmington, Massachusetts, USA; Taconic, N.Y., USA and St. Constance, Quebec, Canada. Animals were housed in microisolator cages inside semi-rigid isolators with sterile food, water and bedding. All experiments were conducted in class II-type safety cabinets (NuAire, Plymouth, Minn., USA), and according to protocols approved by the Canadian Council for Animal Care (Ottawa, Ontario, Canada).

Grafting surgeries were carried out in mice anesthetized with halothane. All incisions and grafted areas in the animals were treated with an antibiotic cream such as Polysporin™ and Sofra-tulle ™ antibiotic dressing (Hoechst-Roussel Canada Inc., Montreal, Quebec, Canada). These were then covered with a layer of petroleum jelly impregnated gauze and kept in position with a flexible adhesive strip.

Cell and tissue culture media, a-modified Eagle's with Earl's salts was purchased from Cellgro. This media is supplemented with the following antibiotics: 0.05 mg/ml gentamycin, 100 µg/ml streptomycin and 100 U/ml penicillin, purchased from Gibco, Ontario, Canada.

Example 1

Initial Viral Extraction from Clinically Excised Human Warts

Clinically excised human anogenital wart tissues were obtained from a local hospital (kindly supplied by Dr. Ferenczy, Jewish General Hospital, Montreal, Quebec, Canada). The collected warts were placed in plastic test tubes, kept on dry ice and transported to our laboratories. The clinical samples were, weighed, minced into small pieces (~1–2 mm squares) and homogenized with a Polytron™ in cold phosphate buffered saline (4° C.) to a final volume of about 5 ml/g tissue. The homogenate was centrifuged at 3000 g (4° C.) for 30 min. The resulting pellet was optionally subjected to a second extraction using the same procedure. The collected ($1^{st}$ and/or $2^{nd}$) supernatant was supplemented with 1% (v/v) stock antibiotics; gentamicin, 50 mg/ml, penicillin, 10,000 units/ml, and streptomycin, 10,000 µg/ml (obtained from Gibco, Ontario, Canada), and stored at −80° C. The extracted supernatants were the initial HPV stock for infecting xenografted human skin tissue. For samples too small to be extracted separately, the warts were swabbed (as in Example 5) and their DNA was typed using PCR assay as described in Example 2. Small warts with the same HPV type were pooled. All manipulations of infected human tissue were carried out according Biosafety Level 2 guidelines.

Example 2

HPV Typing of Clinically Excised Human Warts

HPV DNA was isolated from each sample and then used for typing by PCR amplification using HPV type specific primers. The viral supernantant was digested by adding SDS and proteinase K to a final concentration of 0.5% and 0.2 mg/ml respectively and incubated overnight at 55° C. The DNA was extracted from the digested supernatant using an equal volume of Tris-buffered phenol, followed by one extraction with phenol:chloroform:isoamyl alcohol (25:24:1) and one with chloroform:isoamyl alcohol (24:1). The DNA was precipitated with sodium acetate (3M) and cold absolute ethanol. The resultant pellet was washed in 70% ethanol, dried and resuspended in 0.01 M Tris-HCl buffer (pH 8.0). Amplification reactions were performed using 200 ng of the isolated DNA.

All amplification primers used herein are as described in Mant et al. (J. Vir. Meth., 1997, 66:169–178). Specific primers to HPV-6, VdB-6-U/D, amplified a 280 bp fragment including the HPV-6 L2 open reading frame, and specific primers to HPV-11, vdB-11-U/D amplified a 360 bp fragment including the HPV-11 L1 ORF. As positive control for the amplification reactions, primer pair specific to human β-globin DNA were used in each amplification reaction. The amplification reactions were carried out in a Perkin Elmer GeneAmp PCR System 9600 (Perkin Elmer, Norwalk, Conn.), in a 50 µl volume containing, 5 µl of 10×PCR buffer, 6 µl of 25 mM MgCl$_2$, 1 µl 12.5 dNTP mix, 2 µl of each primer at 10M and 5 U/µl of AmpliTaq Gold™ (Applied Biosystems, Mississauga, ONT) using the following conditions: denaturation at 95° C. for 10 min, followed by 40 cycles of denaturation at 95° C. for 30 sec, annealing at 58° C. for 30 sec and extension at 72° C. for 1 min, with a final extension at 72° C. for 5 min. The amplification products were analyzed by electrophoresis on a 1% agarose gel and visualized with 0.5% ethidium bromide.

The electrophoresed amplification products are shown in FIG. 1, bands of 280 bp and 360 bp corresponding to the vdB-6 and vdB-11 primers confirm the presence of both HPV types 6 and 11 in the clinical wart extract analyzed in FIG. 1A whereas only single type HPV-6 or -11 were present in individual extracts analyzed in FIG. 1B.

Example 3

Preparation of Human Foreskin

Neonatal foreskins from routine circumcisions were collected at the Tiny Tots Clinic (Kindly supplied by Dr. Katz, Dollard-des-Ormeaux, Quebec, Canada). The samples were placed in alpha-modified Eagle's medium with Earle's salt (obtained from Cellgro), supplemented with antibiotics (0.05 mg/ml gentamycin, 100 U/ml penicillin and 100 µg/ml streptomycin) and transported to our laboratories. All manipulations of human tissue were conducted under a class 11 Bio-safety cabinet (NuAire™, Plymouth, Minn., U.S.A.).

The foreskins were processed by first removing occluded tissue and part of the underlying dermis, the split-thickness foreskin tissue samples were prepared using one of the following means:

A. The foreskin tissue was cut into squares of 1×1 cm without being scarified or meshed.

B. The foreskin tissue was scarified using an aliquot of 70 µl/cm² of initial HPV inoculum and then cut into 1×1 cm squares. The scarified tissue was soaked in an additional aliquot of 30 µl/cm² of the initial inoculum and incubated at 37° C. for 1 hour.

C. The foreskin tissue was scarified as above, meshed in a meshing machine (The Zimmer Skin Graft Mesher™, Zimmer Bureau Regional, Montreal, QC, Canada) then cut into 1×1 cm sizes. The scarified and meshed tissue was soaked in an additional 30 µl/cm² aliquot of the initial inoculum and incubated at 37° C. for 1 hour. Tissue scarification is a technique well known in the art. Briefly, the tissue is scraped with an instrument dipped in a viral suspension, thereby introducing viral particles to non-infected tissue. For the purpose of this invention 70 µl/cm² of the initial inoculum prepared from clinical warts as described hereinabove were used for tissue scarification.

Example 4

Cutaneous and Subcutaneous Grafting of Human Skin Tissue

NIH-bg-nu-xid mice obtained from Charles River Laboratories (Wilmington, Boston, USA) or Taconic (N.Y. USA), were n microisolator cages inside semi-rigid isolators and provided with sterile food, water and bedding. All experiments were carried within class 11-type safety cabinets (NuAire, Plymouth, Minn., USA), according to protocols approved by the Canadian Council for Animal Care (Ottawa, Ont. Canada).

All graft surgeries were carried out on recipient animals anesthetized with halothane. For cutaneous grafting, a 1 cm² area of skin from the laterodorsal area from the recipient animal was carefully removed so as to preserve the underlying fascia and minimize bleeding. The graft was fitted into the receiving bedding and fixed in position with size 6-0 silk suture. The grafted areas were dressed with Polysporin™ antibiotic cream and Sofra-tulle™ antibiotic dressing (Hoechst-Roussel Canada Inc., Montreal, QC, Canada). These were then covered with a layer of petroleum jelly impregnated gauze and kept in position with a flexible adhesive strip. The dressings were kept for 3 weeks with changing every 3–4 days or as necessary. For subcutaneous grafting, the processed foreskin tissues were further cut into squares of 5×5 mm sizes and introduced into subcutaneous space via a small opening in the central dorsal area. These incisions were closed with sterile wound clips.

Starting from day 0 post-grafting, all xenografted animals were given the antibiotic Septra™ in their drinking water at a concentration of 1:800 (v/v). The graft sites were observed for the first sign of wart formation and monitored weekly for growth.

In some experiments, subcutaneous engrafted tissues were exposed 10 weeks after grafting by cutting the recipient animal's skin formed over the graft site and suturing the edges of the recipient animal's skin to the engrafted tissue. This surgical procedure was performed with the xenografted animals under halothane anesthesia. The surgical sites were dressed the same way as for the cutaneously engrafted skin tissue (described hereinabove) until the wounds were securely rejoined.

Grafts sites were examined daily for the development of papillomas or other infections. At the onset of visible papillomas, papilloma size was measured as the product of the length, width and height or its cubic root [geometric mean diameter (GMD)]. For cutaneous papillomas, we have developed a scoring system as follows: (0) normal; (1) roughness; (2) small warts with 1–2 mm in each dimension; (3) large warts >2 mm in any 2 dimension; (4) semi-confluent papillomas covering up to half of the graft surface; (5) confluent papillomas covering >½ of the graft surface; (6) confluent papilloma with dense keratinization.

Example 4A

Papilloma Induction with Mixed HPV in Cutaneous Xenografts (FIG. 2B)

From the 8 sites engrafted cutaneously with meshed human skin tissue inoculated with the initial inoculum containing HPV-6 and -11 (as prepared in Example 1), 6 formed visible papillomas having an estimated GMD of 2.3±0.4 mm (scoring between 2 and 5). The appearance of a cutaneous papilloma is shown in FIG. 2B. No visible papillomas were observed up to 6 months at the 4 sites engrafted cutaneously with non-meshed human skin tissue using the same initial inoculum and experimental conditions.

Example 4B

Papilloma Induction with Single-type HPV in Cutaneous Xenoarafts (FIG. 2C)

Table 1 summarizes the frequency of cutaneous induction with single type HPV-11 or -6 prepared from clinical condylomas.

| type | Mouse survival | Graft survival | Induction frequency |
|------|----------------|----------------|---------------------|
| HPV-11 | 5/7 | 10 | 10/10 (7 wks) |
| HPV-6 | 2/12 | 4 | 1/4 (14 wks) |

The premature deaths of immunodeficient mice were caused by contamination from the clinical extracts not related to HPV infection. In subsequent experiments, we introduced a 30 min centrifugation at 15000 g that minimized premature deaths to less than 30%.

Example 4C

Papilloma Induction with Mixed HPV in Sub-cutaneous Xenografts (FIG. 3)

The 16 sites engrafted subcutaneously with meshed human tissue inoculated with mixed HPV-6 and -11 (as prepared in Example 1) were exposed as described above. Seven weeks post-exposure a total of 5 engrafted sites had visible papillomas. Of these, 4 papillomas demonstrated significant growth within the first 10 weeks of grafting and another one formed papilloma within 7 weeks post-exposure. These exteriorized subcutaneous papillomas showed similar morphology as cutaneous papillomas (FIG. 3). No apparent growth was observed in 10 sites engrafted subcutaneously with non-meshed human skin tissue, in the same time period (a total of 17 weeks). However, with repeated surgery for exposure, limited growth was observed in 3 of these 10 sites, 10 weeks after exposure (20 weeks post-grafting). A possible explanation for this limited growth, is that during surgical exposure, wounding of the tissue occurs. This process probably facilitates papillomavirus infection by mimicking the effect of meshing.

Example 4D

Papilloma Induction with Single-type HPV in Sub-cutaneous Xenoarafts (FIG. 4)

With single type HPV-11-infected sub-cutaneous xenografts, papillomas grow significantly. In comparison, 1st generation single type HPV-6 infected tissues do not have obvious growth in most of the grafts.

In addition to their gross morphological similarity to clinical papillomas, these cutaneous and sub-cutaneous warts induced by either mixed or single type virus share the same histological, cellular and immuno-histochemistry characteristics as shown in FIG. 5.

Example 5

HPV Typing of Xenograft Warts

HPV typing was performed by analyzing the DNA of HPV particles sloughed off from the uppermost layer of the graft site or the visible papillomas, or from extracts of the xenografted warts.

In the case of visible papillomas and non-inoculated engrafted sites (used for negative control), the uppermost layer was swabbed first with a cotton swab moistened with PBS followed by gentle rubbing with a dry swab. DNA was isolated by incubating the swabs overnight at 55° C. in a volume of 0.5 ml of digestion buffer (100 mM NaCl, 10 mM Tris-HCl, 25 mM EDTA, and 0.5% SDS) and proteinase K to a final concentration of 0.2 mg/ml. At the end of the incubation period the swabs were squeezed to remove excess liquid and discarded. DNA was extracted from the digested swab samples using classical methods. Briefly, to the digested swab sample an equal volume of phenol:chloroform:isoamyl alcohol (25:24:1) was added followed by centrifugation at 16000 g for 1 min to separate the phases. The aqueous phase was passed through a Microcon-50 microconcentrator (purchased from Millipore Canada Ltd., following manufacturer's instructions) and the DNA was eluted in 25 $\mu$l of 0.25×Tris-EDTA pH 7.4 buffer. The eluted DNA was digested with the restriction enzyme HindIII (100 U/ul) (purchased from New England Biolabs, following manufacturer's instructions). In the case of wart extracts, the DNA was extracted using the same procedure presented in Example 1 for clinical samples.

Aliquots of 5 $\mu$l of the Hind III digested DNA were co-amplified with the primer pair MY09/MY011 which amplify the ORF region of the L1 gene in HPVs non-specifically, and S-GH20/SPCO04 which amplify a region in the human $\beta$-globin gene that serves as positive control (primer sequences are as described in Mant et al., supra). The results of the visualized amplification products are shown in FIG. 6. Lanes 1 to 3, in which DNA derived from non-infected graft sites is amplified, have an amplification product corresponding only to $\beta$-globin (286 bp). Lanes 4 to 6, in which DNA derived from wart tissue is amplified, show amplification products corresponding to HPV (450 bp) and $\beta$-globin (286 bp).

To identify the HPV type present in swab samples derived from wart tissue, the Hind III digested DNA was amplified using primer pairs specific to HPV types 6, 11, 16, 18 and 31 in different amplification reactions (Mant et al.,supra). The results shown in FIG. 7 confirm the presence of HPV types 6 and 11, and the absence of HPV types 16, 18 and 31 in the DNA isolated from cutaneous wart tissue. Therefore amplification products of the DNA extracted from the swab samples demonstrate the presence of HPV-6 and -11 in the cutaneous papillomas.

DNA isolated from swab samples obtained from the surface of 4 exposed subcutaneous grafts are analyzed by amplification using HPV types 6 and 11 specific primers. The results show the presence of both HPV types 6 and 11 (FIG. 8), and the absence of high-risk HPV-16, -18 and -31 at all 4 sites (data not shown). The results presented in FIG. 9 confirm the propagation of single type HPV-6 or -11 separately.

Example 6

Harvesting of Tissue from 1st Generation Papillomas and Producing HPV Stock for Passaging to 2nd and 3rd Generation Xenografted Animals The xenograft papillomas were surgically excised and the tissue treated according to the method used for clinical samples (described in Example 1). HPV stock was collected from these tissues and the HPV typed (as in Example 1). The harvested stock was used to inoculate meshed human skin tissue for engrafting onto immuno-deficient recipient animals. This produced 2nd generation HPV papillomas. The same procedure was repeated serially to produce 3rd generation papillomas.

The viral stock can be stored in phosphate buffered saline supplemented with antibiotics at 1% v/v of gentamycin (50 mg/ml), penicillin (10,000 U/ml) and streptomycin (10,000 $\mu$l/ml) at a temperature of $-80°$ C.

FIG. 10 shows the gross morphology of a cutaneous papilloma from a second generation xenografted animal, in the early stage of wart growth formation. This demonstrates the successful propagation of human papilloma viral particles isolated from a clinical sample through at least two generations of human xenografted animal models.

HPV-6 and -11 mixture stock extracted from 1st generation cutaneous papillomas (cut) or 2 sequential extracts from sub-cutaneous warts (SC1 and SC2), were used to inoculate meshed human skin tissue for engrafting onto immuno-deficient recipients. The resultant animals are referred to herein as 2nd generation animals. The results are summarized in FIG. 11. The first extract of subcutaneous wart (SC1) and the cutaneous harvested virus (cut) induced papillomas in 80% and 33% of the graft sites respectively (day 77 post-grafting), indicating that the SC1 stock was more infectious. The SC2 stock only induced papillomas at 33% inoculation sites, indicating that most of the infectious viral particles were already collected from the first extraction (SC1). A 1:10 dilution of SC1 failed to induce visible papillomas, suggesting that the model is very sensitive to detect low threshold of infection.

FIG. 12 demonstrates the high frequency of papilloma induction with single type HPV-11 in 2nd and 3rd generation using papillomavirus collected from serial xenograft passage. The reproducibility of sub-cutaneous passage of HPV-11 is shown in FIG. 13. Although HPV-6 single type induced wart formation at lower frequency than HPV-11, it seems that a second passage shows improvement in the induction rate (FIG. 14).

DISCUSSION

The Applicant is the first to provide a highly reproducible xenograft animal model for inducing and forming cutaneous and subcutaneous human papillomas, propagating mixed or single type human papillomavirus, harvesting infectious human papilloma virions and advantageously passaging papilloma virions to papilloma-free human xenografted animals.

This study presents a novel human xenograft animal model for propagating HPV. The invention presents a model in which profound tissue injury and in particular by meshing of human skin tissue prior to engrafting plays a significant role. In the cutaneous engrafted model, visible papillomas were induced only in the meshed grafts. In the subcutaneous engrafted model, subcutaneous growth prior to exposure resulted only in the meshed human tissue. With exposure minimal papilloma growth was observed in all the subcutaneous graft sites and only in some non-meshed engrafted tissue following repeated exposure.

The mechanisms underlying the successful induction of human papillomas in injured tissue, particularly meshed tissue are not known but may be due to one or a combination of factors. First, injuring and particularly meshing, may stimulate neoepithelization (Harries et al., 1995, Aust NZ J. Surg., 65:600–603) thus, increasing the population of basal cells which are the target cells for HPV. Second, meshed grafts have a pronounced wound healing process. It is known that during the process of wound healing, an integrin, $\alpha6\beta4$ becomes over-expressed. A recent study (Evander et al., 1997, J. Virol., 71:2449) suggests that this integrin may be a receptor for papillomavirus binding and entry into the host cells and may be an important factor in initiating HPV infection. In addition, this over-expressed integrin may have some other unidentified functions for cellular proliferation and differentiation that may play an important role in papilloma induction.

Therefore, wound healing in response to an injury appears to be a significant factor in the induction of papillomas in human skin tissue and may be an important component in generating animal models for HPV infections. The results presented herein, provide for the first time means to generate a highly reproducible xenografted cutaneous and subcutaneous animal model for HPV. This animal model is useful for propagating and harvesting highly infectious viral particles and passaging human papillomavirus, and for screening potential therapeutic agents.

This work provides a reproducible model of subcutaneous and cutaneous HPV infection in NIH-nu-bg-xid mice, with the capability of forming papillomas having infectious virions in the engrafted wart tissue. The effect of potential candidate agents can be assessed not only in terms of wart growth, but also with respect to viral replication. The ability to propagate the virus through subsequent generations of graft infection obviates the need for clinical human papilloma tissue and provides a means of a continuous and standardized supply of HPV stock for screening purposes.

The selection of the NIH-nu-bg-xid mice has certain advantages over both nu/nu mice and scid mice. As suggested by Stanley, et al. (1997, Antiviral Chem. Chemother, 8:381–400), nu/nu mice may be less immunodeficient than scid and NIH-nu-bg-xid mice and thus not easily allow xenograft tissue to survive and grow. The scid mice are covered in fur thus necessitating removal of the hair before surgery and before evaluating and measuring experimental endpoints. The NIH-nu-bg-xid mouse is essentially hairless and lack functional T-cell, B-cell and NK-cells, thus making it the ideal recipient in this animal model.

All references cited herein, including journal articles or abstracts, published or corresponding U.S. or foreign patent applications, issued U.S. or foreign patents, or any other references, are entirely incorporated by reference herein, including all data, tables, figures, and text presented in the cited references. Additionally, the entire contents of the references cited within the references cited herein are also entirely incorporated by reference.

Reference to known method steps, conventional methods steps, known methods or conventional methods is not in any way an admission that any aspect, description or embodiment of the present invention is disclosed, taught or suggested in the relevant art.

The foregoing description of the specific embodiments will fully reveal the general nature of the invention that others can, by applying knowledge within the skill of the art (including the contents of the references cited herein) readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one skilled in the art.

What is claimed is:

1. A graft mouse model for improving the rate of induction and formation of human papillomas comprising:
    (a) a recipient mouse selected from the group consisting of: severe combined immuno-deficient (SCID) mice, SCID/beige mice, nude mice, and NIH-nu-bg-xid mice, said mouse being grafted with human foreskin tissue, said foreskin tissue having been meshed prior to said grafting; and
    (b) inoculating said grafted foreskin tissue prior to healing with an inoculum of human papillomavirus,
wherein said grafted foreskin is supported by said recipient mouse and is capable of inducing and sustaining growth of said human papillomavirus and harboring at least one papilloma containing infectious viral particles.

2. The model according to claim 1, wherein said meshing is carried out manually.

3. The model according to claim 1, wherein said meshing of the foreskin tissue is accomplished with the use of a meshing machine.

4. The model according to claim 1, wherein said mouse is the NIH-nu-bg-xid mouse.

5. The model according to claim 1, wherein said human papillomavirus is HPV low-risk or high-risk.

6. The model according to claim 5, wherein said low risk human papillomavirus is selected from the group consisting of: type 6, type 11 and type 13.

7. The model according to claim 5, wherein said high risk human papillomavirus is selected from the group consisting of: type 16, type 18, type 35, type 45, type 52 and type 58.

8. The model according to claim 6, wherein said human papillomavirus is low risk type 6 or type 11.

9. A method for producing a graft mouse model for propagating infectious human papilloma viral particles, said method comprising the following steps:
    (a) obtaining foreskin tissue from a human donor and meshing said foreskin;
    (b) grafting said meshed foreskin tissue onto a recipient mouse selected from the group consisting of: severe combined immuno-deficient (SCID) mice, SCID/beige mice, nude mice, and NIH-nu-bg-xid mice
    (c) inoculating said grafted foreskin tissue prior to healing with an inoculum of human papillomavirus; and
    (d) providing sufficient time for said papillomavirus to form in said grafted tissue and to harbor at least one papilloma containing infectious viral particles.

10. The method according to claim 9, wherein said meshing is carried out manually.

11. The method according to claim 9, wherein said meshing of the foreskin tissue is accomplished with the use of a meshing machine.

12. The method according to claim 9, wherein said human papillomavirus is HPV low-risk or high-risk.

13. The method according to claim 12, wherein said low risk human papillomavirus is selected from the group consisting of: type 6, type 11 and type 13.

14. The method according to claim 12, wherein said high risk human papillomavirus is selected from the group consisting of: type 16, type 18, type 35, type 45, type 52 and type 58.

15. The method according to claim 13, wherein said human papillomavirus is low risk type 6 or type 11.

16. The method according to claim 9, wherein said foreskin tissue is inoculated with a papillomavirus suspension, in-situ immediately post-grafting.

17. The method according to claim 16, wherein said post-grafting inoculation in-situ is carried out by overlaying said grafted tissue with a viral suspension, or by injecting the grafted tissue with a viral suspension or a combination thereof.

18. The method according to claim 9, wherein said graft tissue is inserted cutaneously onto said recipient mouse.

19. The method according to claim 9, wherein said graft tissue is inserted subcutaneously onto said recipient mouse such as to form a subcutaneous papilloma.

20. The method according to claim 19, wherein said subcutaneous papilloma is exposed whereby skin covering the apex of the subcutaneous papilloma is cut with a straight incision using surgical scissors, said skin being gently retracted and held back allowing the papilloma to grow outwardly and form a cutaneous papilloma.

21. A method for evaluating the efficacy of a therapeutic agent useful against papilloma virus infection comprising the steps of:

(a) providing a papillomavirus-infected mouse model according to claim 1;

(b) treating said papillomavirus-infected xenografted mouse by administering a candidate therapeutic agent in an appropriate pharmaceutical carrier; and (c) evaluating the efficacy of said therapeutic agent in preventing the appearance, reducing the physiological symptoms or reducing the evidence of said infection in said infected mouse.

* * * * *

UNITED STATES PATENT AND TRADEMARK OFFICE
CERTIFICATE OF CORRECTION

PATENT NO.    : 6,596,924 B1
DATED         : July 22, 2003
INVENTOR(S)   : Jianmin Duan It is certified that error appears in the above-identified patent and that said Letters Patent is hereby corrected as shown below:

<u>Title page,</u>
Item [75], Inventor, "Duan Jianmin" should read -- Jianmin Duan --.

Signed and Sealed this

Thirteenth Day of April, 2004

JON W. DUDAS
*Acting Director of the United States Patent and Trademark Office*